United States Patent
Allen et al.

(10) Patent No.: US 6,620,987 B1
(45) Date of Patent: Sep. 16, 2003

(54) NUCLEIC ACID ENCODING A STARCH R1 PHOSPHORYLATION PROTEIN HOMOLOG FROM MAIZE

(75) Inventors: Stephen M. Allen, Wilmington, DE (US); Karen E. Broglie, Landenberg, PA (US); Karlene H. Butler, Newark, DE (US); Robert F. Cressman, Wilmington, DE (US)

(73) Assignee: E. I. DuPont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/713,273

(22) Filed: Nov. 15, 2000

Related U.S. Application Data

(63) Continuation-in-part of application No. 09/679,933, filed on Oct. 5, 2000, now abandoned, which is a continuation of application No. PCT/US99/07639, filed on Apr. 8, 1999.
(60) Provisional application No. 60/081,143, filed on Apr. 9, 1998.

(51) Int. Cl.[7] .............................. A01H 5/00; A01H 5/10; C12N 5/04; C12N 15/54; C12N 15/82; C12P 21/02
(52) U.S. Cl. .................. 800/298; 435/320.1; 435/71.1; 435/419; 800/284; 536/23.2; 536/23.6
(58) Field of Search ................................ 435/419, 71.1, 435/320.1; 800/284, 298; 536/23.2, 23.6

(56) References Cited

FOREIGN PATENT DOCUMENTS

| WO | 97/11188 A1 | 3/1997 |
|----|-------------|--------|
| WO | 98/27212 | 6/1998 |
| WO | 98/53085 A1 | 11/1998 |
| WO | WO 00/28052 | 5/2000 |

OTHER PUBLICATIONS

Lazar et al., Transforming Growth Factor x: Mutation of Aspartic Acid 47 and Leucine 48 Result in Different Biological Activities, Mar. 1988, Molecular and Cellular Biology, vol. 8, No. 3, pp. 1247–1252.*

Hill et al., Functional Analysis of Conserved Histidines in ADP–Glucose Pyrophosphorylase from *Escherichia coli*, 1998, Biochemical and Bioypisical Research Comm., vol. 244, pp. 573–577.*

EMBL Sequence Database Library Accession No: AC005861, Oct. 27, 1998, X. Lin et al., Arabidopsis thaliana 'IGF' BAC 'F23B24' genomic sequence.

EMBL Sequence Database Library Accession No: AI489255, Mar. 17, 1999, J. Alcala et al., Generation of ESTs from tomato carpel tissue.

EMBL Sequence Database Library Accession No: C71741, Sep. 19, 1997, T. Sasaki et al., Rice cDNA from panicle at flowering stage (970813).

Ruth Lorberth et al., Nature Biotechnology, vol. 16:473–477, May 16, 1998, Inhibition of a starch–granule–bound protein leads to modified starch and repression of cold sweetening.

National Center for Biotechnology Information General Identifier No. 3287270, Jun. 30, 1998, Lorberth, R.

National Center for Biotechnology Information General Identifier No. 7489244, Oct. 8, 1999, Lorberth, R.

* cited by examiner

*Primary Examiner*—Amy J. Nelson
*Assistant Examiner*—Anne Kubelik

(57) ABSTRACT

An isolated polynucleotide comprising a nucleotide sequence encoding a polypeptide having starch R1 phosphorylation activity, or the complement of the nucleotide sequence. Plant transformation and regeneration methods using the polynucleotides. Vectors and recombinant DNA constructs containing the polynucleotides. Cells, plants, and seeds containing the recombinant DNA constructs. Methods for isolating polypeptides having starch R1 phosphorylation activity.

10 Claims, 7 Drawing Sheets

```
SEQ ID NO:16   MSG-------------------------------------------------FSAAANAAAAAERCALAF--RA
SEQ ID NO:18   MSG--------------------------------------------------FSAAA--AAAERCALGLGVHA
SEQ ID NO:20   APASPHFHVIPNLTLFSHLQPIQRNKVIKCGSGKMSQSIFHQTVLCQTVAEHQSKVSS-----------
SEQ ID NO:21   MSNSLGNNLLYQGFLTSTVLEHKSRISPPCVGGN----SLFQQQVI-----------------------
               1                                                                    60

SEQ ID NO:16   RPAASSPAKRQQQPQPASLRRSGGQRRP---TTLSASSR--GPVVPRAVATSADRASPDL
SEQ ID NO:18   RPASPSPA-----LLPPAALRR--GRRLPAATTLAVSRR--SLLAPRAIAASTGRASPGL
SEQ ID NO:20   LEVSANKGKKNLFLAPTNFR---GSRLCVRKRKLTMGRHHHRHVDAVPRAVLTTNLASEL
SEQ ID NO:21   ------SKSPL---STEFR---GNRLKVQKKKIPMEKK--RAFSSSPHAVLTTDTSSEL
               61                                                           120

SEQ ID NO:16   IGKFTLDSNSELQVAVNPAPQGLVSEISLEVTNTSGSLILHWGALRPDKRDWILPSRKPD
SEQ ID NO:18   VGRFTLDANSELKVTLNPAPQGSVVEINLEATNTSGSLILHWGALRPDRGEWLLPSRKPD
SEQ ID NO:20   SGKFNLDGNIELQIAVSSSEPGAARQVDFKVSYNSESLLLHWGVVRDQPGKWVLPSRHPD
SEQ ID NO:21   AEKFSLGGNIELQVDVRPPTSGDVSFVDFQVTNGSDKLFLHWGAVKFGKETWSLPNDRPD
               121                                                          180

SEQ ID NO:16   GTTVYKNRALRTPFVKSGDNSTLRIEIDDPGVHAIEFLIFDETQNKWFKNNGQNFQVQFQ
SEQ ID NO:18   GTTVYKNRALRTPFIKSGDNSTLKIEIDDPAVQAIEFLIFDEARNNWYKNNGQNFQIQLQ
SEQ ID NO:20   GTKNYKSRALRTPFVKSDSGSFLKIEIDDPAAQAIEFLILDEAKNKWFKNNGENFHIKLP
SEQ ID NO:21   GTKVYKNKALRTPFVKSGSNSILRLEIRDTAIEAIEFLIYDEAHDKWIKNNGGNFRVKLS
               181                                                          240
```

FIG. 1A

```
SEQ ID NO:16    SSRHQGTGASGASSSATSTLVPEDLVQIQAYLRWERRGKQSYTPEQEKEEYEAARAELIE
SEQ ID NO:18    ASQYQGQGQTSTATS---STVVPEDLVQIQSYLRWERKGKQSYTPEQEKEEYEAARTELIE
SEQ ID NO:20    VKSKLSQEVS--------VPEDLVQIQAYLRWERKGKQMYTPEQEKEEYEAARNELLE
SEQ ID NO:21    RKEIRGPDVS--------VPEELVQIQSYLRWERKGKQNYPPEKEKEEYEAARTVLQE
                                                                             300
                241

SEQ ID NO:16    EVNRGVSLEKLRAKLTKAPEAPESDESKSSASRMPIGKLPEDLVQVQAYIRWEQAGKPNY
SEQ ID NO:18    ELNKGVSLEKLRAKLTKAPESEST--VTTKVPEELVQVQAYIRWEKAGKPNY
SEQ ID NO:20    EVARGTSVRDLHARLTKKTKAAEVKEPSVSETK----T-IPDELVQIQAFIRWEKAGKPNY
SEQ ID NO:21    EIARGASIQDIRARLTKNDKSQSKEEPLHVTK----SDIPDDLAQAQAYIRWEKAGKPNY
                                                                             360
                301

SEQ ID NO:16    PPEKQLVEFEEARKELQAEVDKGISIDQLRQKILKGNIESKVSKQLKNKKYFSVERIQRK
SEQ ID NO:18    APEKQLVEFEEARKELQSELDKGTSVEQLRNKILKGNIETKVSKQLKDKKYFSVERIQRK
SEQ ID NO:20    SREQQLMEFEEARKELLEELEKGASLDAIRKKIVKGEIQTKVAKQLKTKKYFRAERIQRK
SEQ ID NO:21    PPEKQIEELEEARRELQLELEKGITLDELRKTITKGEIKTKVEKHLK-RSSFAVERIQRK
                                                                             420
                361

SEQ ID NO:16    KRDITQLLSK--HKHTLVEDKVEVVPKQPTVLDLFTKSLHEKDGCEVLSRKLFKFGDKEI
SEQ ID NO:18    KRDIVQLLKK--HKPTVMEAQVET-PKQPTVLDLFTKSLQEQDNCEVLSRKLFKFGDKEI
SEQ ID NO:20    KRDLMQLINR--NVAQNIVEQVIDAPKALTVIEHYANAREEYESGPVLNKTIYKLGDNYL
SEQ ID NO:21    KRDFGHLINKYTSSPAVQVQKVLEEPPALSKIKLYAKEKEEQIDDPILNKKIFKVDDGEL
                                                                             480
                421
```

FIG. 1B

```
                    *     *****  *  ** *****   *  ** *  *  * **   *    ** **
SEQ ID NO:16        LAISTKVQNKTEVHLATNHTDPLILHWSLAKNAGEWKAPSPNILPSGSTLLDKACETEFT
SEQ ID NO:18        LGITTVALGKTKVHLATNYMEPLILHWLATNYMEPLILHWALSKENGEWQAPPSSILPSGSSLLDKACETSFS
SEQ ID NO:20        LVLVTKDAGKIKVHLATDSKKPFTLHWALSRTSEEWLVPPETALPPGSVTMNEAAETPFK
SEQ ID NO:21        LVLVAKSSGKTKVHLATDLNQPITLHWALSKSPGEWMVPPSSILPPGSIILDKAAETPFS
                481                                                          540

***       *  ***           *  *** **  *   ***       *
SEQ ID NO:16        KSELDGLHYQV--VEIELDDGGYKGMPFVLRSGETWKKNNGSDFFLDFSTHDVRNIKLKG
SEQ ID NO:18        EYELNGLHCQV--VEIELDDGGYKGMPFVLRSGETWMKNNGSDFYLDFSTKVAKNTK--D
SEQ ID NO:20        AGSSSHPSYEVQSLDIEVDDDTFKGIPFVILSDGEWIKNNGSNFYIEFGG---KKQKQKD
SEQ ID NO:21        ASSSDGLTSKVQSLDIVIEDGNFVGMPFVLLSGEKWIKNQGSDFYVGFSA--ASKLALKA
                541                                                          600

*  ***  *    ************* ***   ** ***   *    * *** *
SEQ ID NO:16        NGDAGKGTAKALLERIADLEEDAQRSLMHRFNIAADLADQARDAGLLGIVGLFVWIRFMA
SEQ ID NO:18        TGDAGKGTAEALLERIADLEEDAQRSLMHRFNIAADLVDQARDNGLLGLIGIFVWIGFMA
SEQ ID NO:20        FGN-GKGTAKFLLNKIAEMESEAQKSFMHRFNIASDLIDEAKNAGQLGLAGILVWMRFMA
SEQ ID NO:21        AGD-GSGTAKSLLDKIADMESEAQKSFMHRFNIAADLIEDATSAGELGFAGILVWMRFMA
                601                                                          660

*****  ********************* ***  *** *  ******************
SEQ ID NO:16        TRQLTWNKNYNVKPREISKAQDRFTDDLENMYKAYPQYREILRMIMAAVGRGGEGDVGQR
SEQ ID NO:18        TRQLIWNKNYNVKPREISKAQDRFTDDLENMYRTYPQYQEILRMIMSAVGRGGEGDVGQR
SEQ ID NO:20        TRQLIWNKNYNVKPREISKAQDRLTDLLQDVYANYPQYREIVRMILSTVGRGGEGDVGQR
SEQ ID NO:21        TRQLIWNKNYNVKPREISKAQDRLTDLLQNAFTSHPQYREILRMIMSTVGRGGEGDVGQR
                661                                                          720
```

FIG. 1C

```
SEQ ID NO:16  ************ ********** ***** *** **** *** *
SEQ ID NO:18           IRDEILVIQRNNDCKGGMMEEWHQKLHNNTSPDDVVICQALIDYIKSDFDISVYWDTLNK
SEQ ID NO:20           IRDEILVIQRNNDCKGGMMEEWHQKLHNNTSPDDVVICQALLDYIKSDFDTGVYWDTLKK
SEQ ID NO:21           IRDEILVIQRNNDCKGGMMEEWHQKLHNNTSPDDVVICQALIDYINSDFDIGVYWKALND
                       IRDEILVIQRNNDCKGGMMQEWHQKLHNNTSPDDVVICQALIDYIKSDFDLGVYWKTLNE
                                                                                   780

SEQ ID NO:16  *********** ** ******* ** *********************
SEQ ID NO:18           NGITKERLLSYDRAIHSEPNFRSEQKAGLLRDLGNYMRSLKAVHSGADLESAIASCMGYK
SEQ ID NO:20           GGITKERLLSYDRPIHSEPNFRSEQKDSLLRDLGNYMRSLKAVHSGADLESAIATCMGYK
SEQ ID NO:21           NRITKERLLSYDRAIHSEPNFRRDQKEGLLRDLGNYMRTLKAVHSGADLESAISNCMGYK
                       NGITKERLLSYDRAIHSEPNFRGDQKGGLLRDLGHYMRTLKAVHSGADLESAIANCMGYK
                                                                                   840

SEQ ID NO:16  *** ******* ****** ***        **      **       **  ** **
SEQ ID NO:18           SEGEGFMVGVQINPVKGLPSGFPELLEFVLEHVEDKSAEPLLEGLLEARVELRPLLLDSR
SEQ ID NO:20           SEGEGFMVGVQINPVKGLPSGFPKLLEFILDHVEDKSARPLLGGLLEARAELHPLLLGSP
SEQ ID NO:21           SEGQGFMVGVKINPVPGLPTGFPELLEFVMEHVEEKNVEPLLEGLLEARQELQPSLSKSQ
                       TEGEGFMVGVQINPVSGLPSGFQDLLHFVLDHVEDKNVETLLERLLEARELLEARELRPLLKPN
                                                                                   900

SEQ ID NO:16  *  *** **                 ******  ************ **
SEQ ID NO:18           ERMKDLIFLDIALDSTFRTAIERSYEELNDAAPEKIMYFISLVLENLALSIDDNEDILYC
SEQ ID NO:20           ERMKDLIFLDIALDSTFRTAVERSYEELNNVEPEKIMYFISLVLENLALSTDDNEDILYC
SEQ ID NO:21           SRLKDLIFLDVALDSTVRTAVERSYEELNNAGPEKIMYFISLVLENLALSSDDNEDLIYC
                       NRLKDLLFLDIALDSTVRTAVERGYEELNNANPEKIMYFISLVLENLALSVDDNEDLVYC
                                                                                   960
```

FIG. 1D

```
SEQ ID NO:16    LKGWNQALEMAKQKDDQWALYAKAFLDRNRLALASKGEQYHNMMQPSAEYLGSLLSIDQW
SEQ ID NO:18    LKGWNQAVEMAKQKNNQWALYAKAFLDRTRLALASKGEQYYNLMQPSAEYLGSLLNIDQW
SEQ ID NO:20    LKGWDVALSMCKIKDTHWALYAKSVLDRTRLALTNKAHLYQEILQPSAEYLGSLLGVDKW
SEQ ID NO:21    LKGWNQALSMSNGGDNHWALFAKAVLDRTRLALASKAEWYHHLLQPSAEYLGSILGVDQW
                961                                                         1020

SEQ ID NO:16    AVNIFTEEIIRGGSAATLSALLNRFDPVLRNVAHLGSWQVISPVEVSGYVVVDELLAVQ
SEQ ID NO:18    AVNIFTEEIIRGGSAATLSALLNRIDPVLRNVAQLGSWQVISPVEVSGYIVVVDELLAVQ
SEQ ID NO:20    AVEIFTEEIIRAGSAASLSTLLNRLDPVLRKTAHLGSWQVISPVETVGYVEVVDELLTVQ
SEQ ID NO:21    ALNIFTEEIIRAGSAASLSSLLNRLDPVLRKTANLGSWQIISPVEAVGYVVVVDELLSVQ
                1021                                                        1080

SEQ ID NO:16    NKSYDKPTILVAKSVKGEEEIPDGVVGVITPDMPDVLSHVSVRARNSKVLFATCFDHTTL
SEQ ID NO:18    NKSYDKPTILVAKSVKGEEEIPDGVVGVITPDMPDVLSHVSVRARNCKVLFATCFDPNTL
SEQ ID NO:20    NKSYERPTILIANSVKGEEEIPDGTVAVLTPDMPDVLSHVSVRARNSKVCFATCFDPNIL
SEQ ID NO:21    NEIYEKPTILVAKSVKGEEEIPDGAVALITPDMPDVLSHVSVRARNGKVCFATCFDPNIL
                1081                                                        1140

SEQ ID NO:16    SELEGYDQKLFSFKPTSADITYREITESELQQSSSPNAEVGHAVPSISLAKKKFLGKYAI
SEQ ID NO:18    SELQGHDGKVFSEKPTSADITYREIPESELQ-SGSLNAEAGQAVPSVSLVKKKFLGKYAI
SEQ ID NO:20    ANLQEYKGKLLRLKPTSADVVYSEVKEGEFIDDKSTQLKDVGSVSPISLARKKFSGRYAV
SEQ ID NO:21    ADLQAKEGRILLLKPTPSDIIYSEVNEIEL--QSSSNLVEAETSATLRLVKKQFGGCYAI
                1141                                                        1200
```

FIG. 1E

```
SEQ ID NO:16    SAEEFSEEMVGAKSRNIAYLKGKVPSWVGVPTSVAIPFGTFEKVLSDGLNKEVAQSIEKL
SEQ ID NO:18    SAEEFSEEMVGAKSRNVAYLKGKVPSWVGVPTSVAIPFGTFEKVLSDEINKEVAQTIQML
SEQ ID NO:20    SSEEFTGEMVGAKSRNISYLKGKVASWIGIPTSVAIPFGVFEHVLSDKPNQAVAERVNNL
SEQ ID NO:21    SADEFTSEMVGAKSRNIAYLKGKVPSSVGIPTSVALPFGVFEKVLSDDINQVAKELQIL
                                                                          1260

SEQ ID NO:16    KIRLAQEDFSALGEIRKVVLNLTAPMQLVNELKERMLGSGMPWPGDEGDKRWEQAWMAIK
SEQ ID NO:18    KGKLAQDDFSALGEIRKTVLNLTAPTQLIKELKEKMLGSGMPWPGDEGDQRWEQAWMAIK
SEQ ID NO:20    KKKLTEGDFSVLKEIRETVLQLNAPSQLVEELKTKMKSSGMPWPGDEGEQRWEQAWIAIK
SEQ ID NO:21    MKKLSEGDFSALGEIRTTVLDLSAPAQLVKELKEKMQGSGMPWPGDEGPKRWEQAWMAIK
                                                                          1320

SEQ ID NO:16    KVWASKWNERAYFSTRKVKLDHEYLSMAVLVQEVVNADYAFVIHTTNPSSGDSSEIYAEV
SEQ ID NO:18    KVWASKWNERAYFSTRKVKLDHEYLSMAVLVQEIVNADYAFVIHTTNPSSGDSSEIYAEV
SEQ ID NO:20    KVWGSKWNERAYFSTRKVKLDHDYLSMAVLVQEVINADYAFVIHTTNPASGDSSEIYAEV
SEQ ID NO:21    KVWASKWNERAYFSTRKVKLDHDYLCMAVLVQEIINADYAFVIHTTNPSSGDDSEIYAEV
                                                                          1380

SEQ ID NO:16    VKGLGETLVGAYPGRAMSFVCKKDDLDSPKLLGYPSKPIGLFIRQSIIFRSDSNGEDLEG
SEQ ID NO:18    VKGLGETLVGAYPGRAMSFVCKKNDLDSPKVLGFPSKPIGVFIKRSIIFRSDSNGEDLEG
SEQ ID NO:20    VKGLGETLVGAYPGRALSFICKKRDLNSPQVLGYPSKPVGLFIRQSIIFRSDSNGEDLEG
SEQ ID NO:21    VRGLGETLVGAYPGRALSFICKKKDLNSPQVLGYPSKPIGLFIKRSIIFRSDSNGEDLEG
                                                                          1440
```

FIG. 1F

```
              ****  **********     *        ** *    *    ******* *** **
SEQ ID NO:16  YAGAGLYDSVPMDEEDEVVLDYTTDPLIVDRGFRSSILSSIARAGHAIEELYGSPQDVEG
SEQ ID NO:18  YAGARLYDSVPMDEEDEVIVDYNNGPLITDQGFQKSNLPSIAPAGHAIEELYGSPQDVEG
SEQ ID NO:20  YAGAGLYDSVPMDEAEKVVLDYSSDKLILDGSFRQSILSSIARAGNEIEELYGTPQDIEG
SEQ ID NO:21  YAGAGLYDSVPMDEEEKVVIDYSSDPLITDGNFRQTILSNIARAGHAIEELYGSPQDIEG
              1441                                                   1500

** **********
SEQ ID NO:16  VVKDGKIYVVQTRPQM
SEQ ID NO:18  AVKEGKLYVVVQTRPQM
SEQ ID NO:20  VIKDGKVYVVVQTRPQM
SEQ ID NO:21  VVRDGKIYVVVQTRPQM
              1501          1516
```

FIG. 1G

SEQUENCE LISTING

```
<160> NUMBER OF SEQ ID NOS: 21

<210> SEQ ID NO 1
<211> LENGTH: 490
<212> TYPE: DNA
<213> ORGANISM: Arabidopsis thaliana
<220> FEATURE:
<221> NAME/KEY: unsure
<222> LOCATION: (418)
<223> OTHER INFORMATION: n = a, c, g or t
<220> FEATURE:
<221> NAME/KEY: unsure
<222> LOCATION: (429)
<223> OTHER INFORMATION: n = a, c, g or t
<220> FEATURE:
<221> NAME/KEY: unsure
<222> LOCATION: (456)
<223> OTHER INFORMATION: n = a, c, g or t
<220> FEATURE:
<221> NAME/KEY: unsure
<222> LOCATION: (473)
<223> OTHER INFORMATION: n = a, c, g or t
<220> FEATURE:
<221> NAME/KEY: unsure
<222> LOCATION: (485)
<223> OTHER INFORMATION: n = a, c, g or t
<220> FEATURE:
<221> NAME/KEY: unsure
<222> LOCATION: (487)
<223> OTHER INFORMATION: n = a, c, g or t

<400> SEQUENCE: 1
```

-continued

```
gttgaagaaa agaatgtaga gccacttctt gagggtttgc ttgaagctcg tcaagagcta      60
aggccacttc tgctgaagtc ccatgaccgc ctcaaggatc tgttattctt ggacctcgct     120
cttgattcta ctgtcagaac agcgattgaa agaggatatg agcaattgaa tgatgctgga     180
cctgagaaaa tcatgtactt catcagccta gttcttgaaa atcttgccct ctcttcagat     240
gacaatgaag accttatata ctgcttgaag ggatggcaat tgccctcga catgtgcaag     300 agcaaaaaag atcactgggc tctgtatgca aaatctgttc ttgacagaag cccgactagc     360
actggcaagc aaagctgaag aggtaccttg aaattctgca accatcggct gaatatcntg     420
gatctgtcnt ggagtcgatc agtccggctg ttaatntatt actggaagaa atnattcgag     480 ctggntntgc                                                            490
```

<210> SEQ ID NO 2
<211> LENGTH: 161
<212> TYPE: PRT
<213> ORGANISM: Arabidopsis thaliana
<220> FEATURE:
<221> NAME/KEY: UNSURE
<222> LOCATION: (117)
<223> OTHER INFORMATION: Xaa = any amino acid
<220> FEATURE:
<221> NAME/KEY: UNSURE
<222> LOCATION: (127)
<223> OTHER INFORMATION: Xaa = any amino acid
<220> FEATURE:
<221> NAME/KEY: UNSURE
<222> LOCATION: (139)
<223> OTHER INFORMATION: Xaa = any amino acid
<220> FEATURE:
<221> NAME/KEY: UNSURE
<222> LOCATION: (143)
<223> OTHER INFORMATION: Xaa = any amino acid
<220> FEATURE:
<221> NAME/KEY: UNSURE
<222> LOCATION: (152)
<223> OTHER INFORMATION: Xaa = any amino acid
<220> FEATURE:
<221> NAME/KEY: UNSURE
<222> LOCATION: (157)
<223> OTHER INFORMATION: Xaa = any amino acid

<400> SEQUENCE: 2

```
Val Glu Glu Lys Asn Val Glu Pro Leu Leu Gly Leu Leu Glu Ala
 1               5                  10                  15

Arg Gln Glu Leu Arg Pro Leu Leu Lys Ser His Asp Arg Leu Lys
                20                  25                  30

Asp Leu Leu Phe Leu Asp Leu Ala Leu Asp Ser Thr Val Arg Thr Ala
            35                  40                  45

Ile Glu Arg Gly Tyr Glu Gln Leu Asn Asp Ala Gly Pro Glu Lys Ile
 50                  55                  60

Met Tyr Phe Ile Ser Leu Val Leu Glu Asn Leu Ala Leu Ser Ser Asp
 65                  70                  75                  80

Asp Asn Glu Asp Leu Ile Tyr Cys Leu Lys Gly Trp Gln Phe Ala Leu
                85                  90                  95

Asp Met Cys Lys Ser Lys Lys Asp His Trp Ala Leu Tyr Ala Lys Ser
            100                 105                 110

Val Leu Asp Arg Xaa Arg Leu Ala Leu Ala Ser Lys Ala Glu Xaa Tyr
        115                 120                 125

Leu Glu Ile Leu Gln Pro Ser Ala Glu Tyr Xaa Gly Ser Val Xaa Glu
    130                 135                 140

Ser Ile Ser Pro Ala Val Asn Xaa Leu Leu Glu Glu Xaa Ile Arg Ala
145                 150                 155                 160
```

Gly

<210> SEQ ID NO 3
<211> LENGTH: 490
<212> TYPE: DNA
<213> ORGANISM: Curcuma zedoaria
<220> FEATURE:
<221> NAME/KEY: unsure
<222> LOCATION: (466)
<223> OTHER INFORMATION: n = a, c, g or t

<400> SEQUENCE: 3

```
aggtgatgtt ggtcagcgta tccgagatga aatattagtt ttacagagaa acaatgactg    60
caagggagga atgatggagg aatggcatca gaagctacat acaacacta gcccagatga   120
tgttgtgata tgccaggcac ttattgatta tgttaaaagt gattttgaca tcagtgtgta   180
ctgggacagt ttgaataaaa atggaataac caaggaacgt tgttgagct atgatcgtgc   240
tattcattct gaaccaagtt tcaggagaga tcagaaagaa ggtcttttac gtgatctagg   300
aaactacatg aggacgttga aggcagttca ctctggtgca agatctcgag tctgccattg   360
ctacgtgtat gggttacaaa tctgagcgtc aagggcttta tggttggcgt tcaaataaac   420
cccgataggg ggattgccaa ctgggattcc ctgatctaaa ggaaantcaa tccaaaacat   480
gttgaaagat                                                          490
```

<210> SEQ ID NO 4
<211> LENGTH: 144
<212> TYPE: PRT
<213> ORGANISM: Curcuma zedoaria
<220> FEATURE:
<221> NAME/KEY: UNSURE
<222> LOCATION: (114)
<223> OTHER INFORMATION: Xaa = any amino acid
<220> FEATURE:
<221> NAME/KEY: UNSURE
<222> LOCATION: (130)
<223> OTHER INFORMATION: Xaa = any amino acid

<400> SEQUENCE: 4

Gly Asp Val Gly Gln Arg Ile Arg Asp Glu Ile Leu Val Leu Gln Arg
 1               5                  10                  15

Asn Asn Asp Cys Lys Gly Gly Met Met Glu Glu Trp His Gln Lys Leu
            20                  25                  30

His Asn Asn Thr Ser Pro Asp Asp Val Val Ile Cys Gln Ala Leu Ile
        35                  40                  45

Asp Tyr Val Lys Ser Asp Phe Asp Ile Ser Val Tyr Trp Asp Ser Leu
    50                  55                  60

Asn Lys Asn Gly Ile Thr Lys Glu Arg Leu Leu Ser Tyr Asp Arg Ala
65                  70                  75                  80

Ile His Ser Glu Pro Ser Phe Arg Arg Asp Gln Lys Glu Gly Leu Leu
                85                  90                  95

Arg Asp Leu Gly Asn Tyr Met Arg Thr Leu Lys Ala Val His Ser Gly
            100                 105                 110

Ala Xaa Leu Glu Ser Ala Ile Ala Thr Cys Met Gly Tyr Lys Ser Glu
        115                 120                 125

Arg Xaa Gly Phe Met Val Gly Val Gln Ile Asn Pro Asp Arg Gly Ile
    130                 135                 140

<210> SEQ ID NO 5
<211> LENGTH: 487

```
<212> TYPE: DNA
<213> ORGANISM: Brachythecium oxycladon
<220> FEATURE:
<221> NAME/KEY: unsure
<222> LOCATION: (336)
<223> OTHER INFORMATION: n = a, c, g or t
<220> FEATURE:
<221> NAME/KEY: unsure
<222> LOCATION: (408)
<223> OTHER INFORMATION: n = a, c, g or t
<220> FEATURE:
<221> NAME/KEY: unsure
<222> LOCATION: (417)
<223> OTHER INFORMATION: n = a, c, g or t
<220> FEATURE:
<221> NAME/KEY: unsure
<222> LOCATION: (472)
<223> OTHER INFORMATION: n = a, c, g or t

<400> SEQUENCE: 5
cacaccaaga tctggttggt gccaagtctc gtaatatagc caacctgcga ggcaaacttc      60
cctcatggat tcatcttcca acttcagcag cattgccatt tggagttttc gagaaggttt     120
tagcagagcg catcaataag gatgtggcca cagaggttgc tgccctcagc aagcaacttg     180
ctaatggtga ttttagtaag ctccaggatg ctcgtgcaac ggtcttggga ctgaaagcac     240
ctccagcgtt ggttgatgaa ttgaagaaaa ctttgaaaga ctcaggtatg ccgtggcctg     300
gggatgaaag cgaggagaga tggactcaag cctggnctgc aatcaaaagg gtgtgggcct     360
caaaatggaa tgaaagagcc tacttcagta ctcgcaaagc caagatanat cacaagngac     420
ttgtgcatgg caagttatta gttcaagaga tcattcaagg ctgactatgc gntcgtcatt     480
catacca                                                              487

<210> SEQ ID NO 6
<211> LENGTH: 159
<212> TYPE: PRT
<213> ORGANISM: Brachythecium oxycladon
<220> FEATURE:
<221> NAME/KEY: UNSURE
<222> LOCATION: (110)
<223> OTHER INFORMATION: Xaa = any amino acid
<220> FEATURE:
<221> NAME/KEY: UNSURE
<222> LOCATION: (134)
<223> OTHER INFORMATION: Xaa = any amino acid
<220> FEATURE:
<221> NAME/KEY: UNSURE
<222> LOCATION: (137)
<223> OTHER INFORMATION: Xaa = any amino acid
<220> FEATURE:
<221> NAME/KEY: UNSURE
<222> LOCATION: (149)..(150)
<223> OTHER INFORMATION: Xaa = any amino acid
<220> FEATURE:
<221> NAME/KEY: UNSURE
<222> LOCATION: (155)
<223> OTHER INFORMATION: Xaa = any amino acid

<400> SEQUENCE: 6
```

Asp Leu Val Gly Ala Lys Ser Arg Asn Ile Ala Asn Leu Arg Gly Lys
 1               5                  10                  15

Leu Pro Ser Trp Ile His Leu Pro Thr Ser Ala Ala Leu Pro Phe Gly
            20                  25                  30

Val Phe Glu Lys Val Leu Ala Glu Arg Ile Asn Lys Asp Val Ala Thr
        35                  40                  45

Glu Val Ala Ala Leu Ser Lys Gln Leu Ala Asn Gly Asp Phe Ser Lys
    50                  55                  60

Leu Gln Asp Ala Arg Ala Thr Val Leu Gly Leu Lys Ala Pro Pro Ala
 65                  70                  75                  80

Leu Val Asp Glu Leu Lys Lys Thr Leu Lys Asp Ser Gly Met Pro Trp
             85                  90                  95

Pro Gly Asp Glu Ser Glu Glu Arg Trp Thr Gln Ala Trp Xaa Ala Ile
            100                 105                 110

Lys Arg Val Trp Ala Ser Lys Trp Asn Glu Arg Ala Tyr Phe Ser Thr
            115                 120                 125

Arg Lys Ala Lys Ile Xaa His Lys Xaa Leu Val His Gly Lys Leu Leu
        130                 135                 140

Val Gln Glu Ile Xaa Xaa Ala Asp Tyr Ala Xaa Val Ile His Thr
145                 150                 155

<210> SEQ ID NO 7
<211> LENGTH: 503
<212> TYPE: DNA
<213> ORGANISM: Typha latifolia
<220> FEATURE:
<221> NAME/KEY: unsure
<222> LOCATION: (359)
<223> OTHER INFORMATION: n = a, c, g or t
<220> FEATURE:
<221> NAME/KEY: unsure
<222> LOCATION: (380)
<223> OTHER INFORMATION: n = a, c, g or t
<220> FEATURE:
<221> NAME/KEY: unsure
<222> LOCATION: (389)
<223> OTHER INFORMATION: n = a, c, g or t
<220> FEATURE:
<221> NAME/KEY: unsure
<222> LOCATION: (409)
<223> OTHER INFORMATION: n = a, c, g or t
<220> FEATURE:
<221> NAME/KEY: unsure
<222> LOCATION: (429)
<223> OTHER INFORMATION: n = a, c, g or t
<220> FEATURE:
<221> NAME/KEY: unsure
<222> LOCATION: (459)
<223> OTHER INFORMATION: n = a, c, g or t
<220> FEATURE:
<221> NAME/KEY: unsure
<222> LOCATION: (479)
<223> OTHER INFORMATION: n = a, c, g or t
<220> FEATURE:
<221> NAME/KEY: unsure
<222> LOCATION: (481)
<223> OTHER INFORMATION: n = a, c, g or t
<220> FEATURE:
<221> NAME/KEY: unsure
<222> LOCATION: (493)
<223> OTHER INFORMATION: n = a, c, g or t

<400> SEQUENCE: 7
agaaaaacag ttcttcaatt agcacctcca aatccgttgg tagaagagtt gaaggaaaaa      60
atgcatggtg ctggaatgcc atggcctggt gatgaaggtg aatctcggtg ggaacaagca     120 tgatggcaa taaaaaaggt atgggcttca aaatggaatg agagagcata cttcagcacc     180
cgtaaagtaa agttggatca tgactatctt tgcatggctg tcctggtcca agaaattata     240
aatgcaagat tatgcatttg tgatccatac tactaaccca tcaaccggag acgcatcaag     300
agatatatgc tgaggtggtg aaaggactgg gagaagacac tagtgggaag cctacccang     360
gtcgtgcctt aaagcttcan ctgttaagna gaaacgatc ctaaactcnc caaaaggtc     420 ctgggttttnc ccaaaattaa acccaaattg gcctgttcna taaagaaaga tcaatccanc     480
ntcaaaatta agnttcctaa tgg                                             503

```
<210> SEQ ID NO 8
<211> LENGTH: 115
<212> TYPE: PRT
<213> ORGANISM: Typha latifolia
<220> FEATURE:
<221> NAME/KEY: UNSURE
<222> LOCATION: (83)
<223> OTHER INFORMATION: Xaa = any amino acid
<220> FEATURE:
<221> NAME/KEY: UNSURE
<222> LOCATION: (100)
<223> OTHER INFORMATION: Xaa = any amino acid

<400> SEQUENCE: 8

Arg Lys Thr Val Leu Gln Leu Ala Pro Pro Asn Pro Leu Val Glu Glu
 1               5                  10                  15

Leu Lys Glu Lys Met His Gly Ala Gly Met Pro Trp Pro Gly Asp Glu
            20                  25                  30

Gly Glu Ser Arg Trp Glu Gln Ala Trp Met ala Ile Lys Lys Val Trp
        35                  40                  45

Ala Ser Lys Trp Asn Glu Arg Ala Tyr Phe Ser Thr Arg Lys Val Lys
    50                  55                  60

Leu Asp His Asp Tyr Leu Cys Met Ala Val Leu Val Gln Glu Ile Ile
65                  70                  75                  80

Asn Ala Xaa Tyr Ala Phe Val Ile His Thr Thr Asn Pro Ser Thr Gly
                85                  90                  95

Asp Ala Ser Xaa Ile Tyr Ala Glu Val Val Lys Gly Leu Gly Glu Asp
            100                 105                 110

Thr Ser Gly
        115

<210> SEQ ID NO 9
<211> LENGTH: 1633
<212> TYPE: DNA
<213> ORGANISM: Oryza sativa
<220> FEATURE:
<221> NAME/KEY: unsure
<222> LOCATION: (874)
<223> OTHER INFORMATION: n = a, c, g or t
<220> FEATURE:
<221> NAME/KEY: unsure
<222> LOCATION: (876)
<223> OTHER INFORMATION: n = a, c, g or t

<400> SEQUENCE: 9
tggtacctgc taccctgtct gctcttctga atcggattga tcctgttctt aggaatgttg     60
cacagcttgg aagttggcag gttataagcc cagttgaagt atcaggttac attgtagtgg    120
ttgatgaatt gcttgctgtt caaaacaaat cctatgataa accaactatc cttgtggcaa    180
agagtgtcaa gggagaggaa gaaataccag atggagttgt tggtgttatt acacctgata    240
tgccagatgt tctctcccat gtatcagtcc gagcaaggaa ttgcaaggtt ttatttgcaa    300
catgctttga tcctaacacc ttgtctgaac tccaaggaca tgatgggaaa gtgttttcct    360
tcaaacctac ttctgcagat atcacctata gggagattcc agagagtgaa ctgcaatcag    420
gttctctaaa tgcagaagct ggccaggcag tgccatctgt gtcattagtc aagaagaagt    480
ttcttggaaa atatgcaata tcagcagaag aattctctga ggaaatggtt ggggccaagt    540
ctcgcaacgt agcataccctc aaaggaaaag taccctcatg ggttggtgtc cctacatcag    600
ttgcgattcc atttgggacc tttgagaagg ttttgtctga tgaaatcaat aaggaagtcg    660
cgcaaaccat acaaatgctg aagggaaaac ttgctcaaga tgattttagt gctctaggcg    720
```

-continued

```
aaatacggaa aactgttctc aatttaactg ctcctactca actgatcaag gaactgaagg      780
agaagatgct aggctctgga atgccctggc ctggagatga aggtgaccaa cgttgggagc      840
aagcatggat ggcaattaaa aaggtttggg cgtnanaatg gaatgaaaga gcatatttta     900
gcactcgtaa ggtgaagctt gatcatgact acctttccat ggctgtactt gtacaagaaa      960
ttgtcaatgc agactatgcc tttgtcattc atactactaa cccatcatcg ggagattcgt     1020
ctgagatata tgctgaagtg gtgaagggc ttggagaaac acttgtagga gcctatcctg      1080
gtcgcgccat gagctttgta tgtaagaaaa acgaccttga ctctcccaag gtactgggtt     1140
tcccaagcaa gccaattggt gtcttcataa agagatcaat catctttcgt tcggattcca     1200
acggtgagga tttagaaggg tatgctggag caagactgta tgatagtgtc cctatggatg     1260
aggaagatga agtcatagtc gactacaaca acggaccct cattacagat cagggattcc      1320
aaaaatccaa cctcccgagc attgcaccgg ctggtcatgc cattgaggag ctttatgggt     1380
ccccacagga tgttgagggt gcagtgaagg aagggaagct atacgtagta cagacaagac     1440
cacagatgta atctatatgt atattttata gccaagtcaa tcaggcaatg ttgtagagta     1500
agatatacgg gccgtgggac atgtataaca cgttacgccc ttttttttat tatttgcttt     1560
catactcaca atacactaat ttatagggct tattttatcg ccaaaaaaaa aaaaaaaaag     1620
aaaaaaaaaa aaa                                                        1633

<210> SEQ ID NO 10
<211> LENGTH: 482
<212> TYPE: PRT
<213> ORGANISM: Oryza sativa
<220> FEATURE:
<221> NAME/KEY: UNSURE
<222> LOCATION: (291)..(292)
<223> OTHER INFORMATION: Xaa = any amino acid

<400> SEQUENCE: 10

Val Pro Ala Thr Leu Ser Ala Leu Leu Asn Arg Ile Asp Pro Val Leu
 1               5                  10                  15

Arg Asn Val Ala Gln Leu Gly Ser Trp Gln Val Ile Ser Pro Val Glu
                20                  25                  30

Val Ser Gly Tyr Ile Val Val Asp Glu Leu Leu Ala Val Gln Asn
            35                  40                  45

Lys Ser Tyr Asp Lys Pro Thr Ile Leu Val Ala Lys Ser Val Lys Gly
        50                  55                  60

Glu Glu Glu Ile Pro Asp Gly Val Val Gly Val Ile Thr Pro Asp Met
 65                  70                  75                  80

Pro Asp Val Leu Ser His Val Ser Val Arg Ala Arg Asn Cys Lys Val
                 85                  90                  95

Leu Phe Ala Thr Cys Phe Asp Pro Asn Thr Leu Ser Glu Leu Gln Gly
                100                 105                 110

His Asp Gly Lys Val Phe Ser Phe Lys Pro Thr Ser Ala Asp Ile Thr
            115                 120                 125

Tyr Arg Glu Ile Pro Glu Ser Glu Leu Gln Ser Gly Ser Leu Asn Ala
        130                 135                 140

Glu Ala Gly Gln Ala Val Pro Ser Val Ser Leu Val Lys Lys Lys Phe
145                 150                 155                 160

Leu Gly Lys Tyr Ala Ile Ser Ala Glu Glu Phe Ser Glu Glu Met Val
                165                 170                 175

Gly Ala Lys Ser Arg Asn Val Ala Tyr Leu Lys Gly Lys Val Pro Ser
```

180             185             190
Trp Val Gly Val Pro Thr Ser Val Ala Ile Pro Phe Gly Thr Phe Glu
            195             200             205
Lys Val Leu Ser Asp Glu Ile Asn Lys Glu Val Ala Gln Thr Ile Gln
            210             215             220
Met Leu Lys Gly Lys Leu Ala Gln Asp Asp Phe Ser Ala Leu Gly Glu
225             230             235             240
Ile Arg Lys Thr Val Leu Asn Leu Thr Ala Pro Thr Gln Leu Ile Lys
            245             250             255
Glu Leu Lys Glu Lys Met Leu Gly Ser Gly Met Pro Trp Pro Gly Asp
            260             265             270
Glu Gly Asp Gln Arg Trp Glu Gln Ala Trp Met Ala Ile Lys Lys Val
            275             280             285
Trp Ala Xaa Xaa Trp Asn Glu Arg Ala Tyr Phe Ser Thr Arg Lys Val
            290             295             300
Lys Leu Asp His Asp Tyr Leu Ser Met Ala Val Leu Val Gln Glu Ile
305             310             315             320
Val Asn Ala Asp Tyr Ala Phe Val Ile His Thr Thr Asn Pro Ser Ser
            325             330             335
Gly Asp Ser Ser Glu Ile Tyr Ala Glu Val Val Lys Gly Leu Gly Glu
            340             345             350
Thr Leu Val Gly Ala Tyr Pro Gly Arg Ala Met Ser Phe Val Cys Lys
            355             360             365
Lys Asn Asp Leu Asp Ser Pro Lys Val Leu Gly Phe Pro Ser Lys Pro
            370             375             380
Ile Gly Val Phe Ile Lys Arg Ser Ile Ile Phe Arg Ser Asp Ser Asn
385             390             395             400
Gly Glu Asp Leu Glu Gly Tyr Ala Gly Ala Arg Leu Tyr Asp Ser Val
            405             410             415
Pro Met Asp Glu Glu Asp Glu Val Ile Val Asp Tyr Asn Asn Gly Pro
            420             425             430
Leu Ile Thr Asp Gln Gly Phe Gln Lys Ser Asn Leu Pro Ser Ile Ala
            435             440             445
Pro Ala Gly His Ala Ile Glu Glu Leu Tyr Gly Ser Pro Gln Asp Val
            450             455             460
Glu Gly Ala Val Lys Glu Gly Lys Leu Tyr Val Val Gln Thr Arg Pro
465             470             475             480
Gln Met

<210> SEQ ID NO 11
<211> LENGTH: 2080
<212> TYPE: DNA
<213> ORGANISM: Glycine max

<400> SEQUENCE: 11
aaataatgta cttcattagc ttggttcttg aaaatctcgc actttcatcg gatgacaatg      60
aagatcttat ctactgtttg aagggatggg atgttgcctt aagcatgtgc aagattaaag     120
atactcattg gcattgtac gcaaaatcag tccttgacag aacccgtctt gcactaacaa      180
acaaggctca tttataccag gaaattctgc aaccatcggc agaatatctt ggatcactgc     240
ttggcgtgga caaatgggcc gtggaaatat ttactgaaga aattatccgt gctggatctg     300
ctgcttcttt gtctactctt ctaaatcgac tggatcctgt gctccgaaag acagctcatc     360
ttggaagctg gcaggttatt agcccagttg aaactgttgg atatgttgag gtcatagatg     420

```
agttgcttgc tgttcaaaac aaatcatatg agcgacctac aattttgata gccaagagtg      480
tgagaggaga ggaagaaatt ccagatggta cagttgctgt cctgacacct gatatgcccg      540
atgtcctatc ccatgtatct gtacgagcaa gaaatagcaa ggtgtgtttt gctacatgct      600
ttgatcccaa tatcctggct aacctccaag aaaataaagg aaagcttttg cgcttaaagc      660
caacatctgc tgatgtagtt tatagtgagg tcaaggaagg tgagttaatt gatgacaaat      720
caactcaact caaagatgtt ggttctgtgt cacccatatc tctggcccga aagaagttta      780
gtggtagata tgctgtctca tctgaagaat tcactggtga atggttgga gctaaatctc        840 gtaatatctc ttatttaaaa gggaaagtag cttcttggat tggaattcct acctcggttg      900
ccataccatt tggagttttc gaacatgttc tttctgataa accaaaccag gcagtggctg      960
agagggtcaa taatttgaaa agaagttaa ttgagggaga cttcagtgtt ctcaaggaga       1020
ttcgtgaaac agttctacaa ttgaatgcac catcccattt ggtagaggag ttgaaaacta      1080
aaatgaagag ttctggaatg ccgtggccgg gtgatgaagg tgaacaacga tgggagcaag      1140
cttggatagc tataaaaaag gtgtggggct ctaagtggaa tgaaagagca tacttcagca      1200
caagaaaagt gaaactcgac cacgaatatc tttccatggc agtccttgtt caagaagtga      1260
taaatgctga ctatgctttt gtcatccaca caactaaccc tgcctctgga gattcatcgg      1320
aaatatatgc tgaggtggta aagggacttg agaaacact ggttggagct tatccaggtc       1380
gtgctttgag ttttatctgc aagaaacgtg atttgaactc tcctcaggtc ttaggtaatc      1440
ctagcaaacc tgtcggccta tttataagac ggtcaattat ttttcgatct gattccaatg      1500
gtgaagatct agaaggtaat gatggtgcag gtcattatga cagtgtccca atgggtgaac      1560
ccgagaaggt ggtgcttgat tattcttcag acaaactgat ccttgatggc agttttcgcc      1620
agtcaatctt gtccagcatt gcccgtgcag gaaatgaaat tgaagagttg tatggcactc      1680
ctcaggacat tgaaggtgtc atcaaggatg gaaaagtcta tgttgtccag accagaccac      1740
aaatgtagac ctccatacct atgtctttta agccaactac ctcaactatg ttctatgttc      1800
attcccgtgc aacatggcgt tcaaacgtg gccgtggcag cttctgcgag tttaagagta      1860
acccgcggga ttaccaaatt tggccttata gatttattac acgtgatata ttgaaaatta      1920
aggaataatt tataagtgta taaacatgga ataatgtaaa ttaattaaaa aattagatgg      1980
tcttattctt tttccctact atatatattg tatgtactta cttcttccta attaaaattg      2040
ctattcaaag taaaaaaaaa aaaggggggcg ccggtaccca                            2080
```

<210> SEQ ID NO 12
<211> LENGTH: 581
<212> TYPE: PRT
<213> ORGANISM: Glycine max
<400> SEQUENCE: 12

```
Ile Met Tyr Phe Ile Ser Leu Val Leu Glu Asn Leu Ala Leu Ser Ser
  1               5                  10                  15

Asp Asp Asn Glu Asp Leu Ile Tyr Cys Leu Lys Gly Trp Asp Val Ala
             20                  25                  30

Leu Ser Met Cys Lys Ile Lys Asp Thr His Trp Ala Leu Tyr Ala Lys
         35                  40                  45

Ser Val Leu Asp Arg Thr Arg Leu Ala Leu Thr Asn Lys Ala His Leu
     50                  55                  60

Tyr Gln Glu Ile Leu Gln Pro Ser Ala Glu Tyr Leu Gly Ser Leu Leu
 65                  70                  75                  80
```

-continued

```
Gly Val Asp Lys Trp Ala Val Glu Ile Phe Thr Glu Ile Ile Arg
                85                  90                  95

Ala Gly Ser Ala Ala Ser Leu Ser Thr Leu Leu Asn Arg Leu Asp Pro
            100                 105                 110

Val Leu Arg Lys Thr Ala His Leu Gly Ser Trp Gln Val Ile Ser Pro
        115                 120                 125

Val Glu Thr Val Gly Tyr Val Glu Val Ile Asp Glu Leu Leu Ala Val
    130                 135                 140

Gln Asn Lys Ser Tyr Glu Arg Pro Thr Ile Leu Ile Ala Lys Ser Val
145                 150                 155                 160

Arg Gly Glu Glu Glu Ile Pro Asp Gly Thr Val Ala Val Leu Thr Pro
                165                 170                 175

Asp Met Pro Asp Val Leu Ser His Val Ser Val Arg Ala Arg Asn Ser
            180                 185                 190

Lys Val Cys Phe Ala Thr Cys Phe Asp Pro Asn Ile Leu Ala Asn Leu
        195                 200                 205

Gln Glu Asn Lys Gly Lys Leu Leu Arg Leu Lys Pro Thr Ser Ala Asp
    210                 215                 220

Val Val Tyr Ser Glu Val Lys Glu Gly Glu Leu Ile Asp Asp Lys Ser
225                 230                 235                 240

Thr Gln Leu Lys Asp Val Gly Ser Val Ser Pro Ile Ser Leu Ala Arg
                245                 250                 255

Lys Lys Phe Ser Gly Arg Tyr Ala Val Ser Ser Glu Phe Thr Gly
            260                 265                 270

Glu Met Val Gly Ala Lys Ser Arg Asn Ile Ser Tyr Leu Lys Gly Lys
        275                 280                 285

Val Ala Ser Trp Ile Gly Ile Pro Thr Ser Val Ala Ile Pro Phe Gly
    290                 295                 300

Val Phe Glu His Val Leu Ser Asp Lys Pro Asn Gln Ala Val Ala Glu
305                 310                 315                 320

Arg Val Asn Asn Leu Lys Lys Lys Leu Ile Glu Gly Asp Phe Ser Val
                325                 330                 335

Leu Lys Glu Ile Arg Glu Thr Val Leu Gln Leu Asn Ala Pro Ser His
            340                 345                 350

Leu Val Glu Glu Leu Lys Thr Lys Met Lys Ser Ser Gly Met Pro Trp
        355                 360                 365

Pro Gly Asp Glu Gly Glu Gln Arg Trp Glu Gln Ala Trp Ile Ala Ile
    370                 375                 380

Lys Lys Val Trp Gly Ser Lys Trp Asn Glu Arg Ala Tyr Phe Ser Thr
385                 390                 395                 400

Arg Lys Val Lys Leu Asp His Glu Tyr Leu Ser Met Ala Val Leu Val
                405                 410                 415

Gln Glu Val Ile Asn Ala Asp Tyr Ala Phe Val Ile His Thr Thr Asn
            420                 425                 430

Pro Ala Ser Gly Asp Ser Ser Glu Ile Tyr Ala Glu Val Val Lys Gly
        435                 440                 445

Leu Gly Glu Thr Leu Val Gly Ala Tyr Pro Gly Arg Ala Leu Ser Phe
    450                 455                 460

Ile Cys Lys Lys Arg Asp Leu Asn Ser Pro Gln Val Leu Gly Asn Pro
465                 470                 475                 480

Ser Lys Pro Val Gly Leu Phe Ile Arg Arg Ser Ile Ile Phe Arg Ser
                485                 490                 495

Asp Ser Asn Gly Glu Asp Leu Glu Gly Asn Asp Gly Ala Gly His Tyr
```

```
                   500             505             510
Asp Ser Val Pro Met Gly Glu Pro Glu Lys Val Val Leu Asp Tyr Ser
            515                 520                 525

Ser Asp Lys Leu Ile Leu Asp Gly Ser Phe Arg Gln Ser Ile Leu Ser
        530                 535                 540

Ser Ile Ala Arg Ala Gly Asn Glu Ile Glu Glu Leu Tyr Gly Thr Pro
545                 550                 555                 560

Gln Asp Ile Glu Gly Val Ile Lys Asp Gly Lys Val Tyr Val Val Gln
                565                 570                 575

Thr Arg Pro Gln Met
            580

<210> SEQ ID NO 13
<211> LENGTH: 517
<212> TYPE: DNA
<213> ORGANISM: Glycine max
<220> FEATURE:
<221> NAME/KEY: unsure
<222> LOCATION: (371)
<223> OTHER INFORMATION: n = a, c, g or t
<220> FEATURE:
<221> NAME/KEY: unsure
<222> LOCATION: (494)
<223> OTHER INFORMATION: n = a, c, g or t

<400> SEQUENCE: 13
aaggtacagc caagttcttg ttgaataaaa tagcggaaat ggaaagtgag gcacaaaagt       60
ccttcatgca tcgatttaac attgcatcgg atttgataga tgaagctaaa aatgctggtc      120
aacaaggtct tgcggggatt ttggtgtgga tgagattcat ggctactagg cagctcatat      180
ggaacaaaaa ttacaatgtg aagccacgtg agataagtaa agcacaggat aggcttacag      240
acttgctcca ggatgtttat gcaagttacc cacagtatag ggaaattgtg aggatgatct      300
tgtcgactgt tggtcgtgga ggtgaaggag atgtcggaca gaggattcgg gatgaaatcc      360
ttgttatcca ngagaaataa tgattgtaaa ggtggaatga tggaggaatg gcaccagaaa      420
ttacacaata atactagtcc tgatgatgtt gtaatctgtc aagcactaat tgattatata      480
aatagtgact ttgntattgg tgtttactgg caaacat                               517

<210> SEQ ID NO 14
<211> LENGTH: 171
<212> TYPE: PRT
<213> ORGANISM: Glycine max
<220> FEATURE:
<221> NAME/KEY: UNSURE
<222> LOCATION: (123)
<223> OTHER INFORMATION: Xaa = any amino acid
<220> FEATURE:
<221> NAME/KEY: UNSURE
<222> LOCATION: (164)
s<223> OTHER INFORMATION: Xaa = any amino acid

<400> SEQUENCE: 14

Gly Thr Ala Lys Phe Leu Leu Asn Lys Ile Ala Glu Met Glu Ser Glu
1               5                   10                  15

Ala Gln Lys Ser Phe Met His Arg Phe Asn Ile Ala Ser Asp Leu Ile
            20                  25                  30

Asp Glu Ala Lys Asn Ala Gly Gln Gln Gly Leu Ala Gly Ile Leu Val
        35                  40                  45

Trp Met Arg Phe Met Ala Thr Arg Gln Leu Ile Trp Asn Lys Asn Tyr
    50                  55                  60

Asn Val Lys Pro Arg Glu Ile Ser Lys Ala Gln Asp Arg Leu Thr Asp
```

```
                65                  70                  75                  80
Leu Leu Gln Asp Val Tyr Ala Ser Tyr Pro Gln Tyr Arg Glu Ile Val
                        85                  90                  95
Arg Met Ile Leu Ser Thr Val Gly Arg Gly Gly Glu Gly Asp Val Gly
                100                 105                 110
Gln Arg Ile Arg Asp Glu Ile Leu Val Ile Xaa Arg Asn Asn Asp Cys
            115                 120                 125
Lys Gly Gly Met Met Glu Glu Trp His Gln Lys Leu His Asn Asn Thr
        130                 135                 140
Ser Pro Asp Asp Val Val Ile Cys Gln Ala Leu Ile Asp Tyr Ile Asn
145                 150                 155                 160
Ser Asp Phe Xaa Ile Gly Val Tyr Trp Gln Thr
                165                 170

<210> SEQ ID NO 15
<211> LENGTH: 4846
<212> TYPE: DNA
<213> ORGANISM: Zea mays

<400> SEQUENCE: 15
ccacgcgtcc ggcttcatct tgctgatcgt gtccgtggct tcttgatact ccgtgactgt      60
ctccgtccga agcgagtgag caagccgacc aacagcggcg gagattcgct gcaacgtcgg     120
tatcaaaagg tgtccgagcg gttgagattc gcgtgccatg tccggattca gtgccgcggc     180
caacgcagcg gcggctgagc ggtgcgcgct cgcgttccgc gcacggcccg cggcctcctc     240
gccagcgaag cggcagcagc agccgcagcc agcgtccctc cgacgcagcg ggggccagcg     300
ccgccccacg acgtctccg cctctagccg cggcccgt gtgccgcgcg ccgtcgccac       360
gtccgcggac cgcgcgtccc ccgaccttat cggaaagttc acgctggatt ccaactccga     420
gctccaggtc gcagtgaacc cagcgccgca gggtttggtg tcagagatta gcctggaggt     480
gaccaacaca agcggttccc tgattttgca ttggggagcc cttcgcccgg acaagagaga     540
ttggatcctc ccgtccagaa aacctgatgg aacgacagtg tacaagaaca gggctctcag     600
gacaccttt gtaaagtcag gtgataactc cactctaagg attgagatag atgatcctgg       660
ggtgcacgcc attgagttcc tcatctttga cgagacacag aacaaatggt ttaaaaacaa     720
tggccagaat tttcaggttc agttccagtc gagccgccat cagggtactg gtgcatctgg     780
tgcctcctct tctgctactt ctaccttggt gccagaggat cttgtgcaga tccaagctta     840
ccttcggtgg gaagaagggg aaagcagtc atacacacca gagcaagaaa aggaggagta      900
tgaagctgca cgagctgagt taatagagga agtaaacaga ggtgtttctt tagagaagct     960
tcgagctaaa ttgacaaaag cacctgaagc acctgagtcg gatgaaagta atcttctgc     1020
atctcgaatg cccatcggta aacttccaga ggatcttgta caggtgcagg cttatataag    1080
gtgggagcaa gcgggcaagc caaactatcc tcctgagaag caactggtag aatttgagga    1140
agcaaggaag gaactgcagg ctgaggtgga caagggaatc tctattgatc agttgaggca    1200
gaaaattttg aaaggaaaca ttgagagtaa agtttccaag cagctgaaga caagaagta    1260
cttctctgta gaaaggattc agcgcaaaaa gagagatatc acacaacttc tcagtaaaca    1320
taagcataca cttgtggaag ataaagtaga ggttgtacca aaacaaccaa ctgttcttga    1380
tctcttcacc aagtctttac atgagaagga tggctgtgaa gttctaagca gaaagctctt    1440
caagttcggc gataaagaga tactggcaat ttctaccaag gttcaaaata aaacagaagt    1500
tcacttggca acaaaccata ccgacccact tattcttcac tggtctttgg caaaaaatgc    1560
```

```
tggagaatgg aaggcacctt ctccaaatat attgccatct ggttccacat tgctggacaa   1620
ggcgtgtgaa actgaattta ctaaatctga attggatggt ttgcattacc aggttgttga   1680
gatagagctt gatgatggag gatacaaagg aatgccattt gttcttcggt ctggtgaaac   1740
atggaaaaaa aataatggtt ctgattttt cctagatttc agcacccatg atgtcagaaa   1800
tattaagtta aagggcaatg gtgatgctgg taaaggtact gctaaggcat tgctggagag   1860
aatagcagat ctggaggaag atgcccagcg atctcttatg cacagattca atattgcagc   1920
agatctagct gaccaagcca gagatgctgg acttttgggt attgttgggc ttttttgtttg   1980 gattagattc atggctacca ggcaactaac atggaataag aactataatg tgaagccacg   2040
tgagataagc aaagcacagg ataggtttac agatgatctt gagaatatgt acaaagctta   2100
tccacagtac agagagatat taagaatgat aatggctgct gttggtcgcg gaggtgaagg   2160
tgatgttggt caacgcattc gtgatgagat attagtaata cagagaaata atgactgcaa   2220
aggtggaatg atggaagaat ggcaccagaa attgcacaac aatacaagcc cagatgatgt   2280
agtgatatgc caggccttaa ttgattatat caagagtgac tttgatataa gcgtttactg   2340
ggacaccttg aacaaaaatg gcataaccaa agagcgtctc ttgagctatg atcgtgctat   2400
tcattcagaa ccaaatttca gaagtgaaca gaaggcgggt ttactccgtg acctgggaaa   2460
ttacatgaga agcctaaagg ctgtgcattc tggtgctgat cttgaatctg ctatagcaag   2520
ttgtatggga tacaaatcag agggtgaagg tttcatggtt ggtgttcaga tcaatccagt   2580
gaagggttta ccatctggat ttccggagtt gcttgaattt gtgcttgaac atgttgagga   2640
taaatcagcg gaaccacttc ttgagggggct attggaagct cgagttgaac tgcgcccttt   2700
gcttcttgat tcgcgtgaac gcatgaaaga tcttatattt ttggacattg ctcttgattc   2760
taccttcagg acagcaattg aaaggtcata tgaggagctg aatgatgcag ccccagagaa   2820
aataatgtac ttcatcagtc ttgtccttga aaatcttgcg ctttcaattg acgacaatga   2880
agacatcctg tattgtttaa agggatggaa ccaagccttg gaaatggcta agcaaaaaga   2940
cgaccaatgg gcgctctatg ctaaagcatt tcttgacaga aacagacttg cccttgcgag   3000
caagggagaa caataccata atatgatgca gccctctgct gagtatcttg gctcgttact   3060
cagcatagac caatgggcag tcaatatctt cacagaagaa attatacgcg gtggatcagc   3120
tgctactctg tctgctcttc tgaaccgatt tgatcctgtt ttaaggaatg ttgctcacct   3180
cggaagttgg caggttataa gcccggttga agtatcaggt tatgtggttg tggttgatga   3240
gttacttgct gtccagaaca aatcttatga taaaccaacc atccttgtgg caaagagtgt   3300
caagggagag gaagaaatac cagatggagt agttggtgta attacacctg atatgccaga   3360
tgttctgtct catgtgtcag tccgagcaag gaatagcaag gtactgtttg cgacctgttt   3420
tgaccacacc actctatctg aacttgaagg atatgatcag aaactgtttt ccttcaagcc   3480
tacttctgca gatataaccyt ataggagat cacagagagt gaacttcagc aatcaagttc   3540
tccaaatgca gaagttggcc atgcagtacc atctatttca ttggccaaga gaaatttct   3600 tggaaaatat gcaatatcag ccgaagaatt ctctgaggaa atggttgggg ccaagtctcg   3660
gaatatagca tacctcaaag gaaaagtacc ttcatgggtc ggtgtcccaa cgtcagttgc   3720
gataccattt ggcacttttg agaaggtttt gtcagatggg cttaataagg aagtagcaca   3780
gagcatagag aagcttaaga tcagacttgc ccaagaagat tttagtgctc taggtgaaat   3840
aagaaaagtc gtccttaatc ttactgctcc tatgcaattg gttaatgagc tgaaggagag   3900
```

-continued

```
gatgctaggc tctggaatgc cctggcctgg tgatgaagga dacaagcgtt gggagcaagc    3960
atggatggct attaaaaagg tttgggcatc aaaatggaac gaaagagcat attttagcac    4020
acgcaaggtg aaacttgatc atgagtacct ttcgatggct gttctcgtgc aagaagttgt    4080
gaatgcagat tatgcttttg tcattcatac cacaaaccca tcgtctggag attcttctga    4140
gatatatgct gaagtggtga aagggcttgg cgagaccctc gtgggagcct atcctggtcg    4200
tgctatgagc tttgtttgca aaaagatga ccttgactct cccaagttac ttggttaccc     4260
aagcaagcca attggtctct tcataaggca atcaatcatc ttccgttccg actccaacgg    4320
tgaggacctg gaaggttatg ctggagcagg attatatgat agtgtaccga tggatgagga    4380
ggatgaggtt gtacttgatt atacaactga ccctcttata gtagaccgtg gattccgaag    4440
ctcaatcctc tcaagcatag cacgggctgg ccatgccatc gaggagctat atggttctcc    4500
tcaggacgtc gagggagtag tgaaggatgg aaaaatctat gtagtccaga caagaccaca    4560
gatgtagtat gtatgcatct attagacagc tcaataagca ctgttgtacg cttgtatggt    4620
tgggacatat gggcgttatg gcatgtatag ttgtatgcct agatgtacaa cacgtgtact    4680
cgtatatata tatataaatg ctgaaacaag cattggtcct gtactgtagt ttctacattt    4740
cattgtcacc aataattaag tgtactccta tggctgggag tctatgaaaa tggacgtgtt    4800
gacttattgg gtaataaata atttatataa aaaaaaaaaa aaaaag                    4846
```

<210> SEQ ID NO 16
<211> LENGTH: 1469
<212> TYPE: PRT
<213> ORGANISM: Zea mays

<400> SEQUENCE: 16

```
Met Ser Gly Phe Ser Ala Ala Asn Ala Ala Ala Glu Arg Cys
  1               5                  10                  15

Ala Leu Ala Phe Arg Ala Arg Pro Ala Ser Ser Pro Ala Lys Arg
                 20                  25                  30

Gln Gln Gln Pro Gln Pro Ala Ser Leu Arg Arg Ser Gly Gly Gln Arg
         35                  40                  45

Arg Pro Thr Thr Leu Ser Ala Ser Ser Arg Gly Pro Val Val Pro Arg
 50                  55                  60

Ala Val Ala Thr Ser Ala Asp Arg Ala Ser Pro Asp Leu Ile Gly Lys
 65                  70                  75                  80

Phe Thr Leu Asp Ser Asn Ser Glu Leu Gln Val Ala Val Asn Pro Ala
                 85                  90                  95

Pro Gln Gly Leu Val Ser Glu Ile Ser Leu Glu Val Thr Asn Thr Ser
                100                 105                 110

Gly Ser Leu Ile Leu His Trp Gly Ala Leu Arg Pro Asp Lys Arg Asp
         115                 120                 125

Trp Ile Leu Pro Ser Arg Lys Pro Asp Gly Thr Thr Val Tyr Lys Asn
130                 135                 140

Arg Ala Leu Arg Thr Pro Phe Val Lys Ser Gly Asp Asn Ser Thr Leu
145                 150                 155                 160

Arg Ile Glu Ile Asp Asp Pro Gly Val His Ala Ile Glu Phe Leu Ile
                165                 170                 175

Phe Asp Glu Thr Gln Asn Lys Trp Phe Lys Asn Asn Gly Gln Asn Phe
                180                 185                 190

Gln Val Gln Phe Gln Ser Ser Arg His Gln Gly Thr Gly Ala Ser Gly
         195                 200                 205
```

```
Ala Ser Ser Ser Ala Thr Ser Thr Leu Val Pro Glu Asp Leu Val Gln
    210                 215                 220

Ile Gln Ala Tyr Leu Arg Trp Glu Arg Arg Gly Lys Gln Ser Tyr Thr
225                 230                 235                 240

Pro Glu Gln Glu Lys Glu Tyr Glu Ala Ala Arg Ala Glu Leu Ile
                245                 250                 255

Glu Glu Val Asn Arg Gly Val Ser Leu Glu Lys Leu Arg Ala Lys Leu
                260                 265                 270

Thr Lys Ala Pro Glu Ala Pro Glu Ser Asp Glu Ser Lys Ser Ser Ala
    275                 280                 285

Ser Arg Met Pro Ile Gly Lys Leu Pro Glu Asp Leu Gln Val Gln
    290                 295                 300

Ala Tyr Ile Arg Trp Glu Gln Ala Gly Lys Pro Asn Tyr Pro Pro Glu
305                 310                 315                 320

Lys Gln Leu Val Glu Phe Glu Ala Arg Lys Glu Leu Gln Ala Glu
                325                 330                 335

Val Asp Lys Gly Ile Ser Ile Asp Gln Leu Arg Gln Lys Ile Leu Lys
            340                 345                 350

Gly Asn Ile Glu Ser Lys Val Ser Lys Gln Leu Lys Asn Lys Lys Tyr
        355                 360                 365

Phe Ser Val Glu Arg Ile Gln Arg Lys Lys Arg Asp Ile Thr Gln Leu
    370                 375                 380

Leu Ser Lys His Lys His Thr Leu Val Glu Asp Lys Val Glu Val Val
385                 390                 395                 400

Pro Lys Gln Pro Thr Val Leu Asp Leu Phe Thr Lys Ser Leu His Glu
                405                 410                 415

Lys Asp Gly Cys Glu Val Leu Ser Arg Lys Leu Phe Lys Phe Gly Asp
            420                 425                 430

Lys Glu Ile Leu Ala Ile Ser Thr Lys Val Gln Asn Lys Thr Glu Val
        435                 440                 445

His Leu Ala Thr Asn His Thr Asp Pro Leu Ile Leu His Trp Ser Leu
    450                 455                 460

Ala Lys Asn Ala Gly Glu Trp Lys Ala Pro Ser Pro Asn Ile Leu Pro
465                 470                 475                 480

Ser Gly Ser Thr Leu Leu Asp Lys Ala Cys Glu Thr Glu Phe Thr Lys
                485                 490                 495

Ser Glu Leu Asp Gly Leu His Tyr Gln Val Val Glu Ile Glu Leu Asp
            500                 505                 510

Asp Gly Gly Tyr Lys Gly Met Pro Phe Val Leu Arg Ser Gly Glu Thr
        515                 520                 525

Trp Lys Lys Asn Asn Gly Ser Asp Phe Phe Leu Asp Phe Ser Thr His
    530                 535                 540

Asp Val Arg Asn Ile Lys Leu Lys Gly Asn Gly Asp Ala Gly Lys Gly
545                 550                 555                 560

Thr Ala Lys Ala Leu Leu Glu Arg Ile Ala Asp Leu Glu Glu Asp Ala
                565                 570                 575

Gln Arg Ser Leu Met His Arg Phe Asn Ile Ala Ala Asp Leu Ala Asp
            580                 585                 590

Gln Ala Arg Asp Ala Gly Leu Leu Gly Ile Val Gly Leu Phe Val Trp
        595                 600                 605

Ile Arg Phe Met Ala Thr Arg Gln Leu Thr Trp Asn Lys Asn Tyr Asn
    610                 615                 620

Val Lys Pro Arg Glu Ile Ser Lys Ala Gln Asp Arg Phe Thr Asp Asp
```

-continued

```
            625                 630                 635                 640
Leu Glu Asn Met Tyr Lys Ala Tyr Pro Gln Tyr Arg Glu Ile Leu Arg
                    645                 650                 655
Met Ile Met Ala Ala Val Gly Arg Gly Gly Glu Gly Asp Val Gly Gln
            660                 665                 670
Arg Ile Arg Asp Glu Ile Leu Val Ile Gln Arg Asn Asn Asp Cys Lys
                675                 680                 685
Gly Gly Met Met Glu Glu Trp His Gln Lys Leu His Asn Asn Thr Ser
            690                 695                 700
Pro Asp Asp Val Val Ile Cys Gln Ala Leu Ile Asp Tyr Ile Lys Ser
705                 710                 715                 720
Asp Phe Asp Ile Ser Val Tyr Trp Asp Thr Leu Asn Lys Asn Gly Ile
                        725                 730                 735
Thr Lys Glu Arg Leu Leu Ser Tyr Asp Arg Ala Ile His Ser Glu Pro
                    740                 745                 750
Asn Phe Arg Ser Glu Gln Lys Ala Gly Leu Leu Arg Asp Leu Gly Asn
                755                 760                 765
Tyr Met Arg Ser Leu Lys Ala Val His Ser Gly Ala Asp Leu Glu Ser
            770                 775                 780
Ala Ile Ala Ser Cys Met Gly Tyr Lys Ser Glu Gly Glu Gly Phe Met
785                 790                 795                 800
Val Gly Val Gln Ile Asn Pro Val Lys Gly Leu Pro Ser Gly Phe Pro
                        805                 810                 815
Glu Leu Leu Glu Phe Val Leu Glu His Val Glu Asp Lys Ser Ala Glu
                    820                 825                 830
Pro Leu Leu Glu Gly Leu Leu Glu Ala Arg Val Glu Leu Arg Pro Leu
                835                 840                 845
Leu Leu Asp Ser Arg Glu Arg Met Lys Asp Leu Ile Phe Leu Asp Ile
            850                 855                 860
Ala Leu Asp Ser Thr Phe Arg Thr Ala Ile Glu Arg Ser Tyr Glu Glu
865                 870                 875                 880
Leu Asn Asp Ala Ala Pro Glu Lys Ile Met Tyr Phe Ile Ser Leu Val
                        885                 890                 895
Leu Glu Asn Leu Ala Leu Ser Ile Asp Asp Asn Glu Asp Ile Leu Tyr
                    900                 905                 910
Cys Leu Lys Gly Trp Asn Gln Ala Leu Glu Met Ala Lys Gln Lys Asp
                915                 920                 925
Asp Gln Trp Ala Leu Tyr Ala Lys Ala Phe Leu Asp Arg Asn Arg Leu
            930                 935                 940
Ala Leu Ala Ser Lys Gly Glu Gln Tyr His Asn Met Met Gln Pro Ser
945                 950                 955                 960
Ala Glu Tyr Leu Gly Ser Leu Leu Ser Ile Asp Gln Trp Ala Val Asn
                        965                 970                 975
Ile Phe Thr Glu Glu Ile Ile Arg Gly Gly Ser Ala Ala Thr Leu Ser
                    980                 985                 990
Ala Leu Leu Asn Arg Phe Asp Pro Val Leu Arg Asn Val Ala His Leu
                995                 1000                1005
Gly Ser Trp Gln Val Ile Ser Pro Val Glu Val Ser Gly Tyr Val Val
    1010                1015                1020
Val Val Asp Glu Leu Leu Ala Val Gln Asn Lys Ser Tyr Asp Lys Pro
1025                1030                1035                1040
Thr Ile Leu Val Ala Lys Ser Val Lys Gly Glu Glu Ile Pro Asp
                1045                1050                1055
```

-continued

Gly Val Val Gly Val Ile Thr Pro Asp Met Pro Asp Val Leu Ser His
        1060                1065                1070

Val Ser Val Arg Ala Arg Asn Ser Lys Val Leu Phe Ala Thr Cys Phe
    1075                1080                1085

Asp His Thr Thr Leu Ser Glu Leu Glu Gly Tyr Asp Gln Lys Leu Phe
    1090                1095                1100

Ser Phe Lys Pro Thr Ser Ala Asp Ile Thr Tyr Arg Glu Ile Thr Glu
1105                1110                1115                1120

Ser Glu Leu Gln Gln Ser Ser Ser Pro Asn Ala Glu Val Gly His Ala
            1125                1130                1135

Val Pro Ser Ile Ser Leu Ala Lys Lys Lys Phe Leu Gly Lys Tyr Ala
        1140                1145                1150

Ile Ser Ala Glu Glu Phe Ser Glu Glu Met Val Gly Ala Lys Ser Arg
    1155                1160                1165

Asn Ile Ala Tyr Leu Lys Gly Lys Val Pro Ser Trp Val Gly Val Pro
    1170                1175                1180

Thr Ser Val Ala Ile Pro Phe Gly Thr Phe Glu Lys Val Leu Ser Asp
1185                1190                1195                1200

Gly Leu Asn Lys Glu Val Ala Gln Ser Ile Glu Lys Leu Lys Ile Arg
        1205                1210                1215

Leu Ala Gln Glu Asp Phe Ser Ala Leu Gly Glu Ile Arg Lys Val Val
            1220                1225                1230

Leu Asn Leu Thr Ala Pro Met Gln Leu Val Asn Glu Leu Lys Glu Arg
        1235                1240                1245

Met Leu Gly Ser Gly Met Pro Trp Pro Gly Asp Glu Gly Asp Lys Arg
    1250                1255                1260

Trp Glu Gln Ala Trp Met Ala Ile Lys Lys Val Trp Ala Ser Lys Trp
1265                1270                1275                1280

Asn Glu Arg Ala Tyr Phe Ser Thr Arg Lys Val Lys Leu Asp His Glu
            1285                1290                1295

Tyr Leu Ser Met Ala Val Leu Val Gln Glu Val Val Asn Ala Asp Tyr
        1300                1305                1310

Ala Phe Val Ile His Thr Thr Asn Pro Ser Ser Gly Asp Ser Ser Glu
    1315                1320                1325

Ile Tyr Ala Glu Val Val Lys Gly Leu Gly Glu Thr Leu Val Gly Ala
    1330                1335                1340

Tyr Pro Gly Arg Ala Met Ser Phe Val Cys Lys Lys Asp Asp Leu Asp
1345                1350                1355                1360

Ser Pro Lys Leu Leu Gly Tyr Pro Ser Lys Pro Ile Gly Leu Phe Ile
            1365                1370                1375

Arg Gln Ser Ile Ile Phe Arg Ser Asp Ser Asn Gly Glu Asp Leu Glu
        1380                1385                1390

Gly Tyr Ala Gly Ala Gly Leu Tyr Asp Ser Val Pro Met Asp Glu Glu
        1395                1400                1405

Asp Glu Val Val Leu Asp Tyr Thr Thr Asp Pro Leu Ile Val Asp Arg
    1410                1415                1420

Gly Phe Arg Ser Ser Ile Leu Ser Ser Ile Ala Arg Ala Gly His Ala
1425                1430                1435                1440

Ile Glu Glu Leu Tyr Gly Ser Pro Gln Asp Val Glu Gly Val Val Lys
            1445                1450                1455

Asp Gly Lys Ile Tyr Val Val Gln Thr Arg Pro Gln Met
        1460                1465

<210> SEQ ID NO 17
<211> LENGTH: 4576
<212> TYPE: DNA
<213> ORGANISM: Oryza sativa

<400> SEQUENCE: 17

| | | | | | |
|---|---|---|---|---|---|
| cttacagata | ttcgtgcaga | tgagcggatt | ctccgcggca | gctgctgcgg | ccgagcggtg | 60 |
| cgcgctcggc | ctcggcgtcc | acgcgcgccc | cgcctcgccc | tcgccggcgc | tgctcccgcc | 120 |
| ggcggctctc | cgccgcggcc | gccgtctccc | cgcggccacc | accaccctcg | ccgtctcccg | 180 |
| tcggagcctc | ctcgcccctc | cgccatcgc | cgcttccacc | ggccgcgcct | ccccgggcct | 240 |
| tgtcggaagg | ttcaccctgg | atgccaactc | cgagcttaag | gtgacattga | acccagcacc | 300 |
| gcagggttcg | gtggtggaga | tcaatctaga | ggcaactaac | accagcggct | ccctgatact | 360 |
| gcattgggc | gcccttcgcc | cggatagagg | agaatggctc | ctaccatccc | ggaaaccaga | 420 |
| tggcacgaca | gtgtacaaga | acagggctct | taggacgcct | tttataaagt | caggtgataa | 480 |
| ctccacgctg | aaaattgaga | tagatgatcc | tgcagtgcaa | gccattgagt | tcctcatatt | 540 |
| tgatgaggca | cggaataatt | ggtacaaaaa | caatggccag | aatttccaaa | ttcagctaca | 600 |
| agcgagccaa | tatcaagggc | aggtacatc | tactgctact | tcttctactg | tggttccaga | 660 |
| ggatcttgtg | cagatacaat | catatcttcg | gtgggaaaga | aagggaaagc | agtcatatac | 720 |
| acctgagcaa | gagaaggagg | agtatgaagc | agcacgaact | gagttgatag | aggaattaaa | 780 |
| caagggtgtt | tctttggaga | agctacgagc | gaaactgaca | agacacctg | aggcaactga | 840 |
| tagtaatgct | cctgcatctg | aaagcactgt | gactactaaa | gtcccagagg | aacttgtaca | 900 |
| agtccaggct | tacataaggt | gggagaaagc | aggcaagcca | aattatgccc | cagagaagca | 960 |
| attggtcgag | tttgaggaag | caaggaagga | actgcagtct | gagttggata | agggggacctc | 1020 |
| agttgagcag | ttgaggaaca | aaattttgaa | agggaacatt | gagacaaaag | tttccaagca | 1080 |
| gctgaaggac | aaaaaatact | tttctgtgga | aagaattcag | cggaaaaac | gagatattgt | 1140 |
| gcaactactt | aaaaaacaca | agcctactgt | tatggaagcg | caagtagaga | ctcctaaaca | 1200 |
| acccactgtt | ctggatctct | tcacaaagtc | attacaggag | caggataact | gtgaggttct | 1260 |
| aagcagaaag | cttttcaagt | tcggtgacaa | ggagatactg | ggaattacca | ccgttgctct | 1320 |
| aggaaaaacc | aaagttcact | tggcaacaaa | ctatatggag | ccacttatac | ttcactgggc | 1380 |
| gttgtcaaaa | gagaatggag | agtggcaggc | acctccctca | agcatattgc | catctggttc | 1440 |
| atcattgcta | gacaaggcat | gtgaaacttc | attcagtgaa | tatgaattga | atggtctgca | 1500 |
| ttgtcaggtt | gttgagatcg | agcttgacga | tggtggatac | aagcggatgc | cctttgttct | 1560 |
| ccggtctggt | gaaacatgga | tgaaaaataa | tggctctgac | ttttacttgg | atttcagcac | 1620 |
| caaagttgca | aaaaatacaa | aggatactgg | tgatgctggt | aaaggcactg | ctgaggcctt | 1680 |
| gcttgaaaga | atagcagatc | tagaggaaga | tgcccaacga | tctcttatgc | acagattcaa | 1740 |
| tattgcagca | gatctagttg | accaagcgag | agataatgga | ttattgggta | ttattggaat | 1800 |
| ttttgtttgg | attgggttca | tggctacaag | gcaactaata | tggaacaaga | actacaatgt | 1860 |
| gaagccacgt | gagataagca | aagcccaaga | taggtttaca | gatgatcttg | agaatatgta | 1920 |
| cagaacttac | ccacaatatc | aggagatctt | aagaatgata | atgtctgctg | ttggtcgggg | 1980 |
| aggtgaaggt | gatgttggtc | aacgcattcg | tgatgagata | ttagtaatcc | agagaaataa | 2040 |
| tgactgcaaa | ggtggaatga | tggaggagtg | gcaccagaaa | ctgcacaaca | atacaagccc | 2100 |
| agatgatgta | gtgatctgcc | aggccctact | tgattatatc | aagagtgatt | ttgatactgg | 2160 |

-continued

```
tgtttactgg gacaccttga aaaaggtgg tataacaaaa gagcgtctat tgagctatga    2220
tcgaccgatt cattcagagc caaatttcag gagtgaacag aaagatagct tactccgtga    2280
cttgggcaat tatatgagaa gcctcaaggc agtgcattct ggtgctgatc ttgaatctgc    2340
tatagcaact tgcatgggat acaaatcaga gggtgaaggt ttcatggttg gtgttcagat    2400
taatccagtg aagggtttgc catctggatt tcctaaattg cttgaattta tacttgacca    2460
tgttgaggat aaatcagcaa gaccacttct tggagggtta ttggaggctc gagctgaact    2520
acaccctttg ctccttggct ctcctgaacg catgaaggat cttatctttt tagacattgc    2580
tcttgattct actttcagga cagcagtcga aagatcatat gaggagctca ataatgtaga    2640
accagagaaa attatgtact tcatcagtct tgtccttgaa aatcttgctt tatccaccga    2700
cgacaatgaa gatatcctat attgcttaaa gggatggaat caagccgtgg aaatggctaa    2760
acagaaaaac aaccaatggg ctctctatgc taaagcattt ctggacagaa ccagacttgc    2820
ccttgcaagc aagggagaac aatactataa tttgatgcag ccctcagctg aatatcttgg    2880
ctcgttactt aacattgacc aatgggcagt taatatcttt acagaagaaa ttattcgtgg    2940
tggatcagct gctaccctgt ctgctcttct gaatcggatt gatcctgttc ttaggaatgt    3000
tgcacagctt ggaagttggc aggttataag cccagttgaa gtatcaggtt acattgtagt    3060
ggttgatgaa ttgcttgctg ttcaaaacaa atcctatgat aaaccaacta tccttgtggc    3120
aaagagtgtc aagggagagg aagaaatacc agatggagtt gttggtgtta ttacacctga    3180
tatgccagat gttctctccc atgtatcagt ccgagcaagg aattgcaagg ttttatttgc    3240
aacatgcttt gatcctaaca ccttgtctga actccaagga catgatggga agtgttttc    3300
cttcaaacct acttctgcag atatccaccta tagggagatt ccagagagtg aactgcaatc    3360
aggttctcta aatgcagaag ctggccaggc agtgccatct tgtgtcattag tcaagaagaa    3420
gtttcttgga aaatatgcaa tatcagcaga agaattctct gaggaaatgg ttggggccaa    3480
gtctcgcaac gtagcatacc tcaaaggaaa agtaccctca tgggttggtg tccctacatc    3540
agttgcgatt ccatttggga cctttgagaa ggttttgtct gatgaaatca ataaggaagt    3600
cgcgcaaacc atacaaatgc tgaagggaaa acttgctcaa gatgatttta gtgctctagg    3660
cgaaatacgg aaaactgttc tcaatttaac tgctcctact caactgatca aggaactgaa    3720
ggagaagatg ctaggctctg gaatgccctg gcctggagat gaaggtgacc aacgttggga    3780
gcaagcatgg atggcaatta aaaaggtttg ggcgtcaaaa tggaatgaaa gagcatattt    3840
tagcactcgt aaggtgaagc ttgatcatga ctacctttcc atggctgtac ttgtacaaga    3900
aattgtcaat gcagactatg cctttgtcat tcatactact aacccatcat cgggagattc    3960
gtctgagata tatgctgaag tggtgaaagg gcttggagaa acacttgtag gagcctatcc    4020
tggtcgcgcc atgagctttg tatgtaagaa aaacgacctt gactctccca aggtactggg    4080
tttcccaagc aagccaattg gtgtcttcat aaagagatca atcatctttc gttcggattc    4140
caacggtgag gatttagaag ggtatgctgg agcaagactg tatgatagtg tccctatgga    4200
tgaggaagat gaagtcatag tcgactacaa caacggaccc ctcattacag atcagggatt    4260
ccaaaaatcc aacctcccga gcattgcacc ggctggtcat gccattgagg agctttatgg    4320
gtccccacag gatgttgagg gtgcagtgaa ggaagggaag ctatacgtag tacagacaag    4380
accacagatg taatctatat gtatattta gccaagtc aatcaggcaa tgttgtagag    4440
taagatatac gggccgtggg acatgtataa cacgttacgc ccttttttt attatttgct    4500
```

-continued

```
ttcatactca caatacacta atttataggg cttattttat cgccaaaaaa aaaaaaaaa    4560 agaaaaaaaa aaaaaa                                                  4576
```

<210> SEQ ID NO 18
<211> LENGTH: 1457
<212> TYPE: PRT
<213> ORGANISM: Oryza sativa

<400> SEQUENCE: 18

```
Met Ser Gly Phe Ser Ala Ala Ala Ala Ala Glu Arg Cys Ala Leu
  5              10                  15

Gly Leu Gly Val His Ala Arg Pro Ala Ser Pro Ser Pro Ala Leu Leu
              20                  25                  30

Pro Pro Ala Ala Leu Arg Arg Gly Arg Arg Leu Pro Ala Ala Thr Thr
          35                  40                  45

Thr Leu Ala Val Ser Arg Arg Ser Leu Leu Ala Pro Arg Ala Ile Ala
    50                  55                  60

Ala Ser Thr Gly Arg Ala Ser Pro Gly Leu Val Gly Arg Phe Thr Leu
 65                  70                  75                  80

Asp Ala Asn Ser Glu Leu Lys Val Thr Leu Asn Pro Ala Pro Gln Gly
                 85                  90                  95

Ser Val Val Glu Ile Asn Leu Glu Ala Thr Asn Thr Ser Gly Ser Leu
            100                 105                 110

Ile Leu His Trp Gly Ala Leu Arg Pro Asp Arg Gly Glu Trp Leu Leu
        115                 120                 125

Pro Ser Arg Lys Pro Asp Gly Thr Thr Val Tyr Lys Asn Arg Ala Leu
    130                 135                 140

Arg Thr Pro Phe Ile Lys Ser Gly Asp Asn Ser Thr Leu Lys Ile Glu
145                 150                 155                 160

Ile Asp Asp Pro Ala Val Gln Ala Ile Glu Phe Leu Ile Phe Asp Glu
                165                 170                 175

Ala Arg Asn Asn Trp Tyr Lys Asn Asn Gly Gln Asn Phe Gln Ile Gln
            180                 185                 190

Leu Gln Ala Ser Gln Tyr Gln Gly Gln Gly Thr Ser Thr Ala Thr Ser
        195                 200                 205

Ser Thr Val Val Pro Glu Asp Leu Val Gln Ile Gln Ser Tyr Leu Arg
    210                 215                 220

Trp Glu Arg Lys Gly Lys Gln Ser Tyr Thr Pro Glu Gln Glu Lys Glu
225                 230                 235                 240

Glu Tyr Glu Ala Ala Arg Thr Glu Leu Ile Glu Glu Leu Asn Lys Gly
                245                 250                 255

Val Ser Leu Glu Lys Leu Arg Ala Lys Leu Thr Lys Thr Pro Glu Ala
            260                 265                 270

Thr Asp Ser Asn Ala Pro Ala Ser Glu Ser Thr Val Thr Thr Lys Val
        275                 280                 285

Pro Glu Glu Leu Val Gln Val Gln Ala Tyr Ile Arg Trp Glu Lys Ala
    290                 295                 300

Gly Lys Pro Asn Tyr Ala Pro Glu Lys Gln Leu Val Glu Phe Glu Glu
305                 310                 315                 320

Ala Arg Lys Glu Leu Gln Ser Glu Leu Asp Lys Gly Thr Ser Val Glu
                325                 330                 335

Gln Leu Arg Asn Lys Ile Leu Lys Gly Asn Ile Glu Thr Lys Val Ser
            340                 345                 350

Lys Gln Leu Lys Asp Lys Lys Tyr Phe Ser Val Glu Arg Ile Gln Arg
        355                 360                 365
```

```
Lys Lys Arg Asp Ile Val Gln Leu Leu Lys Lys His Lys Pro Thr Val
    370                 375                 380

Met Glu Ala Gln Val Glu Thr Pro Lys Gln Pro Thr Val Leu Asp Leu
385                 390                 395                 400

Phe Thr Lys Ser Leu Gln Glu Gln Asp Asn Cys Glu Val Leu Ser Arg
                405                 410                 415

Lys Leu Phe Lys Phe Gly Asp Lys Glu Ile Leu Gly Ile Thr Thr Val
                420                 425                 430

Ala Leu Gly Lys Thr Lys Val His Leu Ala Thr Asn Tyr Met Glu Pro
            435                 440                 445

Leu Ile Leu His Trp Ala Leu Ser Lys Glu Asn Gly Glu Trp Gln Ala
        450                 455                 460

Pro Pro Ser Ser Ile Leu Pro Ser Gly Ser Ser Leu Leu Asp Lys Ala
465                 470                 475                 480

Cys Glu Thr Ser Phe Ser Glu Tyr Glu Leu Asn Gly Leu His Cys Gln
                485                 490                 495

Val Val Glu Ile Glu Leu Asp Asp Gly Gly Tyr Lys Arg Met Pro Phe
                500                 505                 510

Val Leu Arg Ser Gly Glu Thr Trp Met Lys Asn Asn Gly Ser Asp Phe
        515                 520                 525

Tyr Leu Asp Phe Ser Thr Lys Val Ala Lys Asn Thr Lys Asp Thr Gly
        530                 535                 540

Asp Ala Gly Lys Gly Thr Ala Glu Ala Leu Leu Glu Arg Ile Ala Asp
545                 550                 555                 560

Leu Glu Glu Asp Ala Gln Arg Ser Leu Met His Arg Phe Asn Ile Ala
                565                 570                 575

Ala Asp Leu Val Asp Gln Ala Arg Asp Asn Gly Leu Leu Gly Ile Ile
                580                 585                 590

Gly Ile Phe Val Trp Ile Gly Phe Met Ala Thr Arg Gln Leu Ile Trp
            595                 600                 605

Asn Lys Asn Tyr Asn Val Lys Pro Arg Glu Ile Ser Lys Ala Gln Asp
        610                 615                 620

Arg Phe Thr Asp Asp Leu Glu Asn Met Tyr Arg Thr Tyr Pro Gln Tyr
625                 630                 635                 640

Gln Glu Ile Leu Arg Met Ile Met Ser Ala Val Gly Arg Gly Gly Glu
                645                 650                 655

Gly Asp Val Gly Gln Arg Ile Arg Asp Glu Ile Leu Val Ile Gln Arg
            660                 665                 670

Asn Asn Asp Cys Lys Gly Gly Met Met Glu Glu Trp His Gln Lys Leu
        675                 680                 685

His Asn Asn Thr Ser Pro Asp Asp Val Val Ile Cys Gln Ala Leu Leu
    690                 695                 700

Asp Tyr Ile Lys Ser Asp Phe Asp Thr Gly Val Tyr Trp Asp Thr Leu
705                 710                 715                 720

Lys Lys Gly Gly Ile Thr Lys Glu Arg Leu Leu Ser Tyr Asp Arg Pro
                725                 730                 735

Ile His Ser Glu Pro Asn Phe Arg Ser Glu Gln Lys Asp Ser Leu Leu
            740                 745                 750

Arg Asp Leu Gly Asn Tyr Met Arg Ser Leu Lys Ala Val His Ser Gly
        755                 760                 765

Ala Asp Leu Glu Ser Ala Ile Ala Thr Cys Met Gly Tyr Lys Ser Glu
770                 775                 780
```

-continued

```
Gly Glu Gly Phe Met Val Gly Val Gln Ile Asn Pro Val Lys Gly Leu
785                 790                 795                 800

Pro Ser Gly Phe Pro Lys Leu Leu Glu Phe Ile Leu Asp His Val Glu
            805                 810                 815

Asp Lys Ser Ala Arg Pro Leu Leu Gly Gly Leu Leu Glu Ala Arg Ala
            820                 825                 830

Glu Leu His Pro Leu Leu Leu Gly Ser Pro Arg Met Lys Asp Leu
            835                 840                 845

Ile Phe Leu Asp Ile Ala Leu Asp Ser Thr Phe Arg Thr Ala Val Glu
850                 855                 860

Arg Ser Tyr Glu Glu Leu Asn Asn Val Glu Pro Glu Lys Ile Met Tyr
865                 870                 875                 880

Phe Ile Ser Leu Val Leu Glu Asn Leu Ala Leu Ser Thr Asp Asp Asn
                885                 890                 895

Glu Asp Ile Leu Tyr Cys Leu Lys Gly Trp Asn Gln Ala Val Glu Met
                900                 905                 910

Ala Lys Gln Lys Asn Asn Gln Trp Ala Leu Tyr Ala Lys Ala Phe Leu
                915                 920                 925

Asp Arg Thr Arg Leu Ala Leu Ala Ser Lys Gly Glu Gln Tyr Tyr Asn
    930                 935                 940

Leu Met Gln Pro Ser Ala Glu Tyr Leu Gly Ser Leu Leu Asn Ile Asp
945                 950                 955                 960

Gln Trp Ala Val Asn Ile Phe Thr Glu Glu Ile Ile Arg Gly Gly Ser
                965                 970                 975

Ala Ala Thr Leu Ser Ala Leu Leu Asn Arg Ile Asp Pro Val Leu Arg
                980                 985                 990

Asn Val Ala Gln Leu Gly Ser Trp Gln Val Ile Ser Pro Val Glu Val
            995                 1000                1005

Ser Gly Tyr Ile Val Val Asp Glu Leu Leu Ala Val Gln Asn Lys
    1010                1015                1020

Ser Tyr Asp Lys Pro Thr Ile Leu Val Ala Lys Ser Val Lys Gly Glu
1025                1030                1035                1040

Glu Glu Ile Pro Asp Gly Val Val Gly Val Ile Thr Pro Asp Met Pro
                1045                1050                1055

Asp Val Leu Ser His Val Ser Val Arg Ala Arg Asn Cys Lys Val Leu
            1060                1065                1070

Phe Ala Thr Cys Phe Asp Pro Asn Thr Leu Ser Glu Leu Gln Gly His
        1075                1080                1085

Asp Gly Lys Val Phe Ser Phe Lys Pro Thr Ser Ala Asp Ile Thr Tyr
    1090                1095                1100

Arg Glu Ile Pro Glu Ser Glu Leu Gln Ser Gly Ser Leu Asn Ala Glu
1105                1110                1115                1120

Ala Gly Gln Ala Val Pro Ser Val Ser Leu Val Lys Lys Phe Leu
            1125                1130                1135

Gly Lys Tyr Ala Ile Ser Ala Glu Glu Phe Ser Glu Glu Met Val Gly
        1140                1145                1150

Ala Lys Ser Arg Asn Val Ala Tyr Leu Lys Gly Lys Val Pro Ser Trp
    1155                1160                1165

Val Gly Val Pro Thr Ser Val Ala Ile Pro Phe Gly Thr Phe Glu Lys
    1170                1175                1180

Val Leu Ser Asp Glu Ile Asn Lys Glu Val Ala Gln Thr Ile Gln Met
1185                1190                1195                1200

Leu Lys Gly Lys Leu Ala Gln Asp Asp Phe Ser Ala Leu Gly Glu Ile
```

```
          1205                1210                1215
Arg Lys Thr Val Leu Asn Leu Thr Ala Pro Thr Gln Leu Ile Lys Glu
         1220                1225                1230

Leu Lys Glu Lys Met Leu Gly Ser Gly Met Pro Trp Pro Gly Asp Glu
         1235                1240                1245

Gly Asp Gln Arg Trp Glu Gln Ala Trp Met Ala Ile Lys Lys Val Trp
         1250                1255                1260

Ala Ser Lys Trp Asn Glu Arg Ala Tyr Phe Ser Thr Arg Lys Val Lys
1265               1270                1275                1280

Leu Asp His Asp Tyr Leu Ser Met Ala Val Leu Val Gln Glu Ile Val
              1285                1290                1295

Asn Ala Asp Tyr Ala Phe Val Ile His Thr Thr Asn Pro Ser Ser Gly
         1300                1305                1310

Asp Ser Ser Glu Ile Tyr Ala Glu Val Val Lys Gly Leu Gly Glu Thr
         1315                1320                1325

Leu Val Gly Ala Tyr Pro Gly Arg Ala Met Ser Phe Val Cys Lys Lys
         1330                1335                1340

Asn Asp Leu Asp Ser Pro Lys Val Leu Gly Phe Pro Ser Lys Pro Ile
1345               1350                1355                1360

Gly Val Phe Ile Lys Arg Ser Ile Ile Phe Arg Ser Asp Ser Asn Gly
              1365                1370                1375

Glu Asp Leu Glu Gly Tyr Ala Gly Ala Arg Leu Tyr Asp Ser Val Pro
         1380                1385                1390

Met Asp Glu Glu Asp Glu Val Ile Val Asp Tyr Asn Asn Gly Pro Leu
         1395                1400                1405

Ile Thr Asp Gln Gly Phe Gln Lys Ser Asn Leu Pro Ser Ile Ala Pro
    1410                1415                1420

Ala Gly His Ala Ile Glu Glu Leu Tyr Gly Ser Pro Gln Asp Val Glu
1425               1430                1435                1440

Gly Ala Val Lys Glu Gly Lys Leu Tyr Val Val Gln Thr Arg Pro Gln
              1445                1450                1455
Met

<210> SEQ ID NO 19
<211> LENGTH: 4745
<212> TYPE: DNA
<213> ORGANISM: Glycine max

<400> SEQUENCE: 19
gcaccagcct ctccccattt tcacgtgatt cccaatctca cactcttctc acaccttcaa      60
ccgattcaac gcaacaaagt gataaagtgt ggatccggga agatgagcca gagtatcttc     120
caccagacgg tgctttgtca acgcaaacg gttgcggagc atcaaagtaa ggttagttcc     180
ttggaggtga gtgcgaacaa aggaaagaag aacctctttt tggctcctac aaattttcgc     240
gggagcaggc tgtgtgtgag gaaacgcaaa ttaaccatgg aaggcacca ccaccgccac       300 gttgacgctg ttccacgcgc tgttttaacc accaatctgg cttctgagct ttctgggaag     360
ttcaaccttg acggaaatat tgagttgcag attgctgtta gttcttcaga accaggagct     420
gcaagacaag tagattttaa ggtttcatat aatagtgagt ctctgctttt acattgggga     480
gttgtgcgtg atcagccagg gaagtgggtt cttccttctc gtcacccaga tggaactaaa     540
aattataaga gcagagctct tagaactcct tttgtgaaat ccgactcagg atctttcctt     600
aaaatagaaa ttgacgatcc tgctgcacaa gccattgagt tcctcatact tgatgaggct     660
aagaataagt ggtttaagaa taatggtgag aactttcaca tcaagttacc agtaaaaagc     720
```

-continued

```
aagctatctc aagaagtttc agttcctgaa gaccttgtac agattcaagc atatcttagg      780
tgggaacgaa agggtaagca gatgtacact ccagagcaag agaaggagga atatgaagca      840
gctcggaatg aactattgga ggaagtagcc aggggtactt ctgtgcgaga tctccatgca      900
aggttaacta agaaaactaa agctgccgaa gtaaaggagc cttctgtttc tgaaacaaag      960
accatccctg atgaacttgt acagattcaa gcttttatac gatgggaaaa agctgggaag     1020
cctaactact ctcgggaaca caacttatg gaatttgagg aagcaagaaa agaattgtta      1080
gaagagcttg agaaggggc ttctctggat gcgatacgga agaagattgt caaggagag       1140 atacaaacta aagttgccaa gcaattgaaa accaaaaaat actttcgtgc tgaaagaata     1200
cagaggaaaa agagagattt gatgcagctt atcaaccgaa atgttgcaca aaatatagtt     1260
gaacaagtta tagatgctcc aaaagccttg acagtaattg aacattatgc caatgcaagg     1320
gaagaatatg aaagtggtcc tgttttgaat aagacaatat acaagcttgg tgataattat     1380
cttctggtcc ttgttaccaa ggatgctggc aagattaagg ttcacctagc tacagactcg     1440
aaaaaacctt ttacacttca ctgggcctta tctagaacat ctgaagagtg gttggtacca     1500
cctgaaactg ctctgccccc tggatctgtt actatgaatg aggccgctga acacctttc     1560 aaagctggtt cttcgtctca tccttcttat gaggtccagt ccttggatat agaggttgat     1620
gatgatactt ttaaaggaat acctttttgtc attctgtcgg atggagaatg gataaagaac    1680
aatggatcaa attttttatat tgaatttggt gggaagaagc agaaacagaa ggattttggc    1740
aatggcaaag gtacagccaa gttcttgttg aataaaatag cagaaatgga aagtgaggca    1800
caaaagtcct tcatgcatcg atttaacatt gcatcagatt tgatagatga agccaaaaat    1860
gctggtcaac tgggtcttgc ggggattttg gtgtggatga gattcatggc tacaaggcag    1920
ctcatatgga acaaaaatta caatgtgaag ccacgtgaga taagtaaagc acaggatagg    1980
cttacagact tgctccaaga tgtttatgca aattatccac agtataggga aattgtgagg    2040
atgatcttgt ccactgttgg tcgtggaggt gaaggagatg tcggacagag gattcgggat    2100
gaaatccttg ttatccagag aaataatgat tgcaaaggtg gaatgatgga ggaatggcac    2160
cagaaattac acaataatac tagtcctgat gatgttgtaa tctgtcaggc actaattgat    2220
tatataaata gtgactttga tattggtgtt tactggaaag cattgaatga caatagaata    2280
acaaaagagc ggcttctgag ctatgaccgt gccatccatt ctgaaccaaa ttttaggaga    2340
gatcagaagg aaggtcttct gcgagatctg ggaaactaca tgaggacttt aaaggcagtt    2400
cattccggtg cagatcttga atctgctatt tcaaattgta tgggctacaa atctgagggt    2460
cagggcttca tggtaggggt gaagataaat ccagtgccgg gtttgcctac tggttttcca    2520
gaattacttg agtttgtcat ggaacacgtt gaagagaaga atgttgaacc acttcttgag    2580
gggttgcttg aggctcgtca ggaactccaa ccatcactca gtaaatccca aagtcgtctg    2640
aaagatctta tatttttgga tgttgcccctt gattctacag ttagaacagc agtggaaagg    2700
agttatgagg aattaaacaa tgctggacct gagaaaataa tgtacttcat tagcttggtt    2760
cttgaaaatc tcgcactttc atcggatgac aatgaagatc ttatctactg tttgaaggga    2820
tgggatgttc ccttaagcat gtgcaagatt aaagatactc attgggcatt gtacgcaaaa    2880
tcagtccttg acagaacccg tcttgcacta acaaacaagg ctcatttata ccaggaaatt    2940
ctgcaaccat cggcagaata tcttggatca ctgcttggcg tggacaaatg ggccgtggaa    3000
atatttactg aagaaattat ccgtgctgga tctgctgctt ctttgtctac tcttctaaat    3060
```

-continued

```
cgactggatc ctgtgctccg aaagacagct catcttggaa gctggcaggt tattagtcca    3120
gttgaaactg ttggatatgt tgaggttgta gatgagttgc ttactgttca aaacaaatca    3180
tatgagcgac ctacaatttt gatagccaat agtgtgaaag gagaggaaga aattccagat    3240
ggtacagttg ctgtcctgac acctgatatg cctgatgtcc tatcccatgt ttctgtacga    3300
gcaagaaata gcaaggtgtg ttttgctaca tgctttgatc ccaatatcct ggctaacctc    3360
caagaatata aaggaaagct tttacgctta aagcctacat ctgctgatgt agtttatagt    3420
gaggtgaagg agggtgagtt tattgatgac aaatcaactc aactgaaaga tgttggttct    3480
gtgtcaccca tatctctggc cagaaagaag tttagtggta gatatgctgt ctcatctgaa    3540
gaattcactg tgaaatggt tggagctaaa tctcgtaata tctcttattt aaaagggaaa     3600
gtagcttctt ggattggaat tcctacctca gttgccatac catttggagt ttttgaacat    3660
gttctttctg ataaaccaaa ccaggcagtg gctgagaggg tcaataattt gaaaagaag     3720
ttaactgagg gagacttcag tgttctcaag gagattcgtg aaacagttct acagttgaat    3780
gcaccatccc agttggtaga ggagttgaaa actaaaatga gagttctgg aatgccgtgg    3840
ccgggtgatg aaggtgaaca acgatgggaa caagcttgga tagctataaa aaaggtgtgg    3900
ggctcaaagt ggaatgaaag agcatacttc agcacaagaa aagtgaaact cgaccacgaa    3960
tatctttcca tggcagtcct ggttcaggaa gtgataaatg ctgactatgc ttttgtcatc    4020
cacacaacta accctgcctc tggagattca tcggaaatat atgctgaggt ggtaaaggga    4080
cttggagaaa cactggttgg agcttatcct ggtcgtgctt tgagttttat ctgcaagaaa    4140
cgtgatttga actctcctca ggtcttgggt tatcctagca aacctgtcgg cctatttata    4200
agacagtcaa ttatttccg atctgattcc aatggtgaag atctagaagg ttatgctggt    4260
gcaggtcttt atgacagtgt gccaatggat gaagccgaga aggtggtgct tgattattca    4320
tcagacaaac tgatccttga tggtagtttt cgccagtcaa tcttgtccag cattgcccgt    4380
gcaggaaatg aaattgaaga gttgtatggc actcctcagg acattgaagg tgtcatcaag    4440
gatggcaaag tctatgttgt ccagaccaga ccacaaatgt aaacttgcat acccatgtct    4500
tctaagccac ctacctcaac tatgttcatc cccgagcaac acgtcgtttc aaacgtggcc    4560
gtggcagctt ctgtgagttc aagagtaacc cccggattac caaacatggc cttatagatt    4620
tattacatga tatattgaaa attaaggaat aagtgtataa aaacggaata ttgtaaatta    4680
agaaaaattt agacggtctt atatattctt tttccctact ataaaaaaaa aaaaaaaaaa    4740
aaaaa                                                                4745
```

<210> SEQ ID NO 20
<211> LENGTH: 1493
<212> TYPE: PRT
<213> ORGANISM: Glycine max
<400> SEQUENCE: 20

```
Ala Pro Ala Ser Pro His Phe His Val Ile Pro Asn Leu Thr Leu Phe
  1               5                  10                  15

Ser His Leu Gln Pro Ile Gln Arg Asn Lys Val Ile Lys Cys Gly Ser
             20                  25                  30

Gly Lys Met Ser Gln Ser Ile Phe His Gln Thr Val Leu Cys Gln Thr
         35                  40                  45

Gln Thr Val Ala Glu His Gln Ser Lys Val Ser Ser Leu Glu Val Ser
     50                  55                  60

Ala Asn Lys Gly Lys Lys Asn Leu Phe Leu Ala Pro Thr Asn Phe Arg
 65                  70                  75                  80
```

```
Gly Ser Arg Leu Cys Val Arg Lys Arg Lys Leu Thr Met Gly Arg His
                85                  90                  95

His His Arg His Val Asp Ala Val Pro Arg Ala Val Leu Thr Thr Asn
            100                 105                 110

Leu Ala Ser Glu Leu Ser Gly Lys Phe Asn Leu Asp Gly Asn Ile Glu
            115                 120                 125

Leu Gln Ile Ala Val Ser Ser Ser Glu Pro Gly Ala Ala Arg Gln Val
        130                 135                 140

Asp Phe Lys Val Ser Tyr Asn Ser Glu Ser Leu Leu His Trp Gly
145                 150                 155                 160

Val Val Arg Asp Gln Pro Gly Lys Trp Val Leu Pro Ser Arg His Pro
                165                 170                 175

Asp Gly Thr Lys Asn Tyr Lys Ser Arg Ala Leu Arg Thr Pro Phe Val
                180                 185                 190

Lys Ser Asp Ser Gly Ser Phe Leu Lys Ile Glu Ile Asp Asp Pro Ala
                195                 200                 205

Ala Gln Ala Ile Glu Phe Leu Ile Leu Asp Glu Ala Lys Asn Lys Trp
        210                 215                 220

Phe Lys Asn Asn Gly Glu Asn Phe His Ile Lys Leu Pro Val Lys Ser
225                 230                 235                 240

Lys Leu Ser Gln Glu Val Ser Val Pro Glu Asp Leu Val Gln Ile Gln
                245                 250                 255

Ala Tyr Leu Arg Trp Glu Arg Lys Gly Lys Gln Met Tyr Thr Pro Glu
                260                 265                 270

Gln Glu Lys Glu Glu Tyr Glu Ala Ala Arg Asn Glu Leu Leu Glu Glu
            275                 280                 285

Val Ala Arg Gly Thr Ser Val Arg Asp Leu His Ala Arg Leu Thr Lys
        290                 295                 300

Lys Thr Lys Ala Ala Glu Val Lys Glu Pro Ser Val Ser Glu Thr Lys
305                 310                 315                 320

Thr Ile Pro Asp Glu Leu Val Gln Ile Gln Ala Phe Ile Arg Trp Glu
                325                 330                 335

Lys Ala Gly Lys Pro Asn Tyr Ser Arg Glu Gln Gln Leu Met Glu Phe
            340                 345                 350

Glu Glu Ala Arg Lys Glu Leu Leu Glu Glu Leu Glu Lys Gly Ala Ser
            355                 360                 365

Leu Asp Ala Ile Arg Lys Lys Ile Val Lys Gly Glu Ile Gln Thr Lys
        370                 375                 380

Val Ala Lys Gln Leu Lys Thr Lys Lys Tyr Phe Arg Ala Glu Arg Ile
385                 390                 395                 400

Gln Arg Lys Lys Arg Asp Leu Met Gln Leu Ile Asn Arg Asn Val Ala
                405                 410                 415

Gln Asn Ile Val Glu Gln Val Ile Asp Ala Pro Lys Ala Leu Thr Val
                420                 425                 430

Ile Glu His Tyr Ala Asn Ala Arg Glu Glu Tyr Glu Ser Gly Pro Val
            435                 440                 445

Leu Asn Lys Thr Ile Tyr Lys Leu Gly Asp Asn Tyr Leu Leu Val Leu
450                 455                 460

Val Thr Lys Asp Ala Gly Lys Ile Lys Val His Leu Ala Thr Asp Ser
465                 470                 475                 480

Lys Lys Pro Phe Thr Leu His Trp Ala Leu Ser Arg Thr Ser Glu Glu
                485                 490                 495
```

-continued

```
Trp Leu Val Pro Pro Glu Thr Ala Leu Pro Pro Gly Ser Val Thr Met
            500                 505                 510
Asn Glu Ala Ala Glu Thr Pro Phe Lys Ala Gly Ser Ser His Pro
        515                 520                 525
Ser Tyr Glu Val Gln Ser Leu Asp Ile Glu Val Asp Asp Thr Phe
        530                 535                 540
Lys Gly Ile Pro Phe Val Ile Leu Ser Asp Gly Glu Trp Ile Lys Asn
545                 550                 555                 560
Asn Gly Ser Asn Phe Tyr Ile Glu Phe Gly Lys Lys Gln Lys Gln
                565                 570                 575
Lys Asp Phe Gly Asn Gly Lys Gly Thr Ala Lys Phe Leu Leu Asn Lys
                580                 585                 590
Ile Ala Glu Met Glu Ser Glu Ala Gln Lys Ser Phe Met His Arg Phe
            595                 600                 605
Asn Ile Ala Ser Asp Leu Ile Asp Glu Ala Lys Asn Ala Gly Gln Leu
            610                 615                 620
Gly Leu Ala Gly Ile Leu Val Trp Met Arg Phe Met Ala Thr Arg Gln
625                 630                 635                 640
Leu Ile Trp Asn Lys Asn Tyr Asn Val Lys Pro Arg Glu Ile Ser Lys
                645                 650                 655
Ala Gln Asp Arg Leu Thr Asp Leu Leu Gln Asp Val Tyr Ala Asn Tyr
                660                 665                 670
Pro Gln Tyr Arg Glu Ile Val Arg Met Ile Leu Ser Thr Val Gly Arg
                675                 680                 685
Gly Gly Glu Gly Asp Val Gly Gln Arg Ile Arg Asp Glu Ile Leu Val
            690                 695                 700
Ile Gln Arg Asn Asn Asp Cys Lys Gly Gly Met Met Glu Glu Trp His
705                 710                 715                 720
Gln Lys Leu His Asn Asn Thr Ser Pro Asp Asp Val Val Ile Cys Gln
                725                 730                 735
Ala Leu Ile Asp Tyr Ile Asn Ser Asp Phe Asp Ile Gly Val Tyr Trp
                740                 745                 750
Lys Ala Leu Asn Asp Asn Arg Ile Thr Lys Glu Arg Leu Leu Ser Tyr
                755                 760                 765
Asp Arg Ala Ile His Ser Glu Pro Asn Phe Arg Arg Asp Gln Lys Glu
            770                 775                 780
Gly Leu Leu Arg Asp Leu Gly Asn Tyr Met Arg Thr Leu Lys Ala Val
785                 790                 795                 800
His Ser Gly Ala Asp Leu Glu Ser Ala Ile Ser Asn Cys Met Gly Tyr
                805                 810                 815
Lys Ser Glu Gly Gln Gly Phe Met Val Gly Val Lys Ile Asn Pro Val
                820                 825                 830
Pro Gly Leu Pro Thr Gly Phe Pro Glu Leu Leu Glu Phe Val Met Glu
            835                 840                 845
His Val Glu Glu Lys Asn Val Glu Pro Leu Leu Glu Gly Leu Leu Glu
            850                 855                 860
Ala Arg Gln Glu Leu Gln Pro Ser Leu Ser Lys Ser Gln Ser Arg Leu
865                 870                 875                 880
Lys Asp Leu Ile Phe Leu Asp Val Ala Leu Asp Ser Thr Val Arg Thr
                885                 890                 895
Ala Val Glu Arg Ser Tyr Glu Glu Leu Asn Asn Ala Gly Pro Glu Lys
            900                 905                 910
Ile Met Tyr Phe Ile Ser Leu Val Leu Glu Asn Leu Ala Leu Ser Ser
```

-continued

```
            915                 920                 925
Asp Asp Asn Glu Asp Leu Ile Tyr Cys Leu Lys Gly Trp Asp Val Ala
            930                 935                 940
Leu Ser Met Cys Lys Ile Lys Asp Thr His Trp Ala Leu Tyr Ala Lys
945                 950                 955                 960
Ser Val Leu Asp Arg Thr Arg Leu Ala Leu Thr Asn Lys Ala His Leu
                965                 970                 975
Tyr Gln Glu Ile Leu Gln Pro Ser Ala Glu Tyr Leu Gly Ser Leu Leu
                980                 985                 990
Gly Val Asp Lys Trp Ala Val Glu Ile Phe Thr Glu Ile Ile Arg
                995                 1000                1005
Ala Gly Ser Ala Ala Ser Leu Ser Thr Leu Leu Asn Arg Leu Asp Pro
    1010                1015                1020
Val Leu Arg Lys Thr Ala His Leu Gly Ser Trp Gln Val Ile Ser Pro
1025                1030                1035                1040
Val Glu Thr Val Gly Tyr Val Glu Val Val Asp Glu Leu Leu Thr Val
                1045                1050                1055
Gln Asn Lys Ser Tyr Glu Arg Pro Thr Ile Leu Ile Ala Asn Ser Val
            1060                1065                1070
Lys Gly Glu Glu Glu Ile Pro Asp Gly Thr Val Ala Val Leu Thr Pro
        1075                1080                1085
Asp Met Pro Asp Val Leu Ser His Val Ser Val Arg Ala Arg Asn Ser
        1090                1095                1100
Lys Val Cys Phe Ala Thr Cys Phe Asp Pro Asn Ile Leu Ala Asn Leu
1105                1110                1115                1120
Gln Glu Tyr Lys Gly Lys Leu Leu Arg Leu Lys Pro Thr Ser Ala Asp
            1125                1130                1135
Val Val Tyr Ser Glu Val Lys Glu Gly Glu Phe Ile Asp Asp Lys Ser
                1140                1145                1150
Thr Gln Leu Lys Asp Val Gly Ser Val Ser Pro Ile Ser Leu Ala Arg
            1155                1160                1165
Lys Lys Phe Ser Gly Arg Tyr Ala Val Ser Ser Glu Glu Phe Thr Gly
    1170                1175                1180
Glu Met Val Gly Ala Lys Ser Arg Asn Ile Ser Tyr Leu Lys Gly Lys
1185                1190                1195                1200
Val Ala Ser Trp Ile Gly Ile Pro Thr Ser Val Ala Ile Pro Phe Gly
                1205                1210                1215
Val Phe Glu His Val Leu Ser Asp Lys Pro Asn Gln Ala Val Ala Glu
            1220                1225                1230
Arg Val Asn Asn Leu Lys Lys Lys Leu Thr Glu Gly Asp Phe Ser Val
        1235                1240                1245
Leu Lys Glu Ile Arg Glu Thr Val Leu Gln Leu Asn Ala Pro Ser Gln
1250                1255                1260
Leu Val Glu Glu Leu Lys Thr Lys Met Lys Ser Ser Gly Met Pro Trp
1265                1270                1275                1280
Pro Gly Asp Glu Gly Glu Gln Arg Trp Glu Gln Ala Trp Ile Ala Ile
            1285                1290                1295
Lys Lys Val Trp Gly Ser Lys Trp Asn Glu Arg Ala Tyr Phe Ser Thr
            1300                1305                1310
Arg Lys Val Lys Leu Asp His Glu Tyr Leu Ser Met Ala Val Leu Val
        1315                1320                1325
Gln Glu Val Ile Asn Ala Asp Tyr Ala Phe Val Ile His Thr Thr Asn
    1330                1335                1340
```

```
Pro Ala Ser Gly Asp Ser Ser Glu Ile Tyr Ala Glu Val Val Lys Gly
1345                1350                1355                1360

Leu Gly Glu Thr Leu Val Gly Ala Tyr Pro Gly Arg Ala Leu Ser Phe
            1365                1370                1375

Ile Cys Lys Lys Arg Asp Leu Asn Ser Pro Gln Val Leu Gly Tyr Pro
        1380                1385                1390

Ser Lys Pro Val Gly Leu Phe Ile Arg Gln Ser Ile Ile Phe Arg Ser
    1395                1400                1405

Asp Ser Asn Gly Glu Asp Leu Glu Gly Tyr Ala Gly Ala Gly Leu Tyr
1410                1415                1420

Asp Ser Val Pro Met Asp Glu Ala Glu Lys Val Val Leu Asp Tyr Ser
1425                1430                1435                1440

Ser Asp Lys Leu Ile Leu Asp Gly Ser Phe Arg Gln Ser Ile Leu Ser
            1445                1450                1455

Ser Ile Ala Arg Ala Gly Asn Glu Ile Glu Glu Leu Tyr Gly Thr Pro
            1460                1465                1470

Gln Asp Ile Glu Gly Val Ile Lys Asp Gly Lys Val Tyr Val Val Gln
    1475                1480                1485

Thr Arg Pro Gln Met
    1490

<210> SEQ ID NO 21
<211> LENGTH: 1464
<212> TYPE: PRT
<213> ORGANISM: Solanum tuberosum

<400> SEQUENCE: 21

Met Ser Asn Ser Leu Gly Asn Asn Leu Leu Tyr Gln Gly Phe Leu Thr
1               5                   10                  15

Ser Thr Val Leu Glu His Lys Ser Arg Ile Ser Pro Pro Cys Val Gly
            20                  25                  30

Gly Asn Ser Leu Phe Gln Gln Gln Val Ile Ser Lys Ser Pro Leu Ser
        35                  40                  45

Thr Glu Phe Arg Gly Asn Arg Leu Lys Val Gln Lys Lys Lys Ile Pro
    50                  55                  60

Met Glu Lys Lys Arg Ala Phe Ser Ser Pro His Ala Val Leu Thr
65                  70                  75                  80

Thr Asp Thr Ser Ser Glu Leu Ala Glu Lys Phe Ser Leu Gly Gly Asn
            85                  90                  95

Ile Glu Leu Gln Val Asp Val Arg Pro Pro Thr Ser Gly Asp Val Ser
        100                 105                 110

Phe Val Asp Phe Gln Val Thr Asn Gly Ser Asp Lys Leu Phe Leu His
    115                 120                 125

Trp Gly Ala Val Lys Phe Gly Lys Glu Thr Trp Ser Leu Pro Asn Asp
130                 135                 140

Arg Pro Asp Gly Thr Lys Val Tyr Lys Asn Lys Ala Leu Arg Thr Pro
145                 150                 155                 160

Phe Val Lys Ser Gly Ser Asn Ser Ile Leu Arg Leu Glu Ile Arg Asp
            165                 170                 175

Thr Ala Ile Glu Ala Ile Glu Phe Leu Ile Tyr Asp Glu Ala His Asp
        180                 185                 190

Lys Trp Ile Lys Asn Asn Gly Gly Asn Phe Arg Val Lys Leu Ser Arg
    195                 200                 205
```

```
Lys Glu Ile Arg Gly Pro Asp Val Ser Val Pro Glu Leu Val Gln
    210                 215                 220
Ile Gln Ser Tyr Leu Arg Trp Glu Arg Lys Gly Lys Gln Asn Tyr Pro
225                 230                 235                 240
Pro Glu Lys Glu Lys Glu Glu Tyr Glu Ala Ala Arg Thr Val Leu Gln
                245                 250                 255
Glu Glu Ile Ala Arg Gly Ala Ser Ile Gln Asp Ile Arg Ala Arg Leu
            260                 265                 270
Thr Lys Thr Asn Asp Lys Ser Gln Ser Lys Glu Glu Pro Leu His Val
        275                 280                 285
Thr Lys Ser Asp Ile Pro Asp Asp Leu Ala Gln Ala Gln Ala Tyr Ile
    290                 295                 300
Arg Trp Glu Lys Ala Gly Lys Pro Asn Tyr Pro Glu Lys Gln Ile
305                 310                 315                 320
Glu Glu Leu Glu Glu Ala Arg Arg Glu Leu Gln Leu Glu Leu Glu Lys
                325                 330                 335
Gly Ile Thr Leu Asp Glu Leu Arg Lys Thr Ile Thr Lys Gly Glu Ile
            340                 345                 350
Lys Thr Lys Val Glu Lys His Leu Lys Arg Ser Ser Phe Ala Val Glu
        355                 360                 365
Arg Ile Gln Arg Lys Lys Arg Asp Phe Gly His Leu Ile Asn Lys Tyr
    370                 375                 380
Thr Ser Ser Pro Ala Val Gln Val Gln Lys Val Leu Glu Glu Pro Pro
385                 390                 395                 400
Ala Leu Ser Lys Ile Lys Leu Tyr Ala Lys Glu Lys Glu Glu Gln Ile
                405                 410                 415
Asp Asp Pro Ile Leu Asn Lys Lys Ile Phe Lys Val Asp Asp Gly Glu
            420                 425                 430
Leu Leu Val Leu Val Ala Lys Ser Ser Gly Lys Thr Lys Val His Leu
        435                 440                 445
Ala Thr Asp Leu Asn Gln Pro Ile Thr Leu His Trp Ala Leu Ser Lys
    450                 455                 460
Ser Pro Gly Glu Trp Met Val Pro Ser Ser Ile Leu Pro Pro Gly
465                 470                 475                 480
Ser Ile Ile Leu Asp Lys Ala Ala Glu Thr Pro Phe Ser Ala Ser Ser
                485                 490                 495
Ser Asp Gly Leu Thr Ser Lys Val Gln Ser Leu Asp Ile Val Ile Glu
            500                 505                 510
Asp Gly Asn Phe Val Gly Met Pro Phe Val Leu Leu Ser Gly Glu Lys
        515                 520                 525
Trp Ile Lys Asn Gln Gly Ser Asp Phe Tyr Val Gly Phe Ser Ala Ala
    530                 535                 540
Ser Lys Leu Ala Leu Lys Ala Gly Asp Gly Ser Gly Thr Ala Lys
545                 550                 555                 560
Ser Leu Leu Asp Lys Ile Ala Asp Met Glu Ser Glu Ala Gln Lys Ser
                565                 570                 575
Phe Met His Arg Phe Asn Ile Ala Ala Asp Leu Ile Glu Asp Ala Thr
            580                 585                 590
Ser Ala Gly Glu Leu Gly Phe Ala Gly Ile Leu Val Trp Met Arg Phe
        595                 600                 605
Met Ala Thr Arg Gln Leu Ile Trp Asn Lys Asn Tyr Asn Val Lys Pro
    610                 615                 620
Arg Glu Ile Ser Lys Ala Gln Asp Arg Leu Thr Asp Leu Leu Gln Asn
```

```
                625                 630                 635                 640
Ala Phe Thr Ser His Pro Gln Tyr Arg Glu Ile Leu Arg Met Ile Met
                645                 650                 655
Ser Thr Val Gly Arg Gly Gly Glu Gly Asp Val Gly Gln Arg Ile Arg
                660                 665                 670
Asp Glu Ile Leu Val Ile Gln Arg Asn Asn Asp Cys Lys Gly Gly Met
            675                 680                 685
Met Gln Glu Trp His Gln Lys Leu His Asn Asn Thr Ser Pro Asp Asp
            690                 695                 700
Val Val Ile Cys Gln Ala Leu Ile Asp Tyr Ile Lys Ser Asp Phe Asp
705                 710                 715                 720
Leu Gly Val Tyr Trp Lys Thr Leu Asn Glu Asn Gly Ile Thr Lys Glu
                725                 730                 735
Arg Leu Leu Ser Tyr Asp Arg Ala Ile His Ser Glu Pro Asn Phe Arg
                740                 745                 750
Gly Asp Gln Lys Gly Gly Leu Leu Arg Asp Leu Gly His Tyr Met Arg
                755                 760                 765
Thr Leu Lys Ala Val His Ser Gly Ala Asp Leu Glu Ser Ala Ile Ala
            770                 775                 780
Asn Cys Met Gly Tyr Lys Thr Glu Gly Glu Gly Phe Met Val Gly Val
785                 790                 795                 800
Gln Ile Asn Pro Val Ser Gly Leu Pro Ser Gly Phe Gln Asp Leu Leu
                805                 810                 815
His Phe Val Leu Asp His Val Glu Asp Lys Asn Val Glu Thr Leu Leu
                820                 825                 830
Glu Arg Leu Leu Glu Ala Arg Glu Glu Leu Arg Pro Leu Leu Leu Lys
            835                 840                 845
Pro Asn Asn Arg Leu Lys Asp Leu Leu Phe Leu Asp Ile Ala Leu Asp
850                 855                 860
Ser Thr Val Arg Thr Ala Val Glu Arg Gly Tyr Glu Glu Leu Asn Asn
865                 870                 875                 880
Ala Asn Pro Glu Lys Ile Met Tyr Phe Ile Ser Leu Val Leu Glu Asn
                885                 890                 895
Leu Ala Leu Ser Val Asp Asp Asn Glu Asp Leu Val Tyr Cys Leu Lys
                900                 905                 910
Gly Trp Asn Gln Ala Leu Ser Met Ser Asn Gly Gly Asp Asn His Trp
            915                 920                 925
Ala Leu Phe Ala Lys Ala Val Leu Asp Arg Thr Arg Leu Ala Leu Ala
930                 935                 940
Ser Lys Ala Glu Trp Tyr His His Leu Leu Gln Pro Ser Ala Glu Tyr
945                 950                 955                 960
Leu Gly Ser Ile Leu Gly Val Asp Gln Trp Ala Leu Asn Ile Phe Thr
                965                 970                 975
Glu Glu Ile Ile Arg Ala Gly Ser Ala Ala Ser Leu Ser Ser Leu Leu
            980                 985                 990
Asn Arg Leu Asp Pro Val Leu Arg Lys Thr Ala Asn Leu Gly Ser Trp
            995                 1000                1005
Gln Ile Ile Ser Pro Val Glu Ala Val Gly Tyr Val Val Val Asp
    1010                1015                1020
Glu Leu Leu Ser Val Gln Asn Glu Ile Tyr Glu Lys Pro Thr Ile Leu
1025                1030                1035                1040
Val Ala Lys Ser Val Lys Gly Glu Glu Glu Ile Pro Asp Gly Ala Val
            1045                1050                1055
```

-continued

Ala Leu Ile Thr Pro Asp Met Pro Asp Val Leu Ser His Val Ser Val
          1060            1065            1070

Arg Ala Arg Asn Gly Lys Val Cys Phe Ala Thr Cys Phe Asp Pro Asn
    1075            1080            1085

Ile Leu Ala Asp Leu Gln Ala Lys Glu Gly Arg Ile Leu Leu Leu Lys
    1090            1095            1100

Pro Thr Pro Ser Asp Ile Ile Tyr Ser Glu Val Asn Glu Ile Glu Leu
1105            1110            1115            1120

Gln Ser Ser Ser Asn Leu Val Glu Ala Glu Thr Ser Ala Thr Leu Arg
            1125            1130            1135

Leu Val Lys Lys Gln Phe Gly Gly Cys Tyr Ala Ile Ser Ala Asp Glu
            1140            1145            1150

Phe Thr Ser Glu Met Val Gly Ala Lys Ser Arg Asn Ile Ala Tyr Leu
    1155            1160            1165

Lys Gly Lys Val Pro Ser Ser Val Gly Ile Pro Thr Ser Val Ala Leu
    1170            1175            1180

Pro Phe Gly Val Phe Glu Lys Val Leu Ser Asp Asp Ile Asn Gln Gly
1185            1190            1195            1200

Val Ala Lys Glu Leu Gln Ile Leu Met Lys Lys Leu Ser Glu Gly Asp
            1205            1210            1215

Phe Ser Ala Leu Gly Glu Ile Arg Thr Thr Val Leu Asp Leu Ser Ala
            1220            1225            1230

Pro Ala Gln Leu Val Lys Glu Leu Lys Glu Lys Met Gln Gly Ser Gly
            1235            1240            1245

Met Pro Trp Pro Gly Asp Glu Gly Pro Lys Arg Trp Glu Gln Ala Trp
    1250            1255            1260

Met Ala Ile Lys Lys Val Trp Ala Ser Lys Trp Asn Glu Arg Ala Tyr
1265            1270            1275            1280

Phe Ser Thr Arg Lys Val Lys Leu Asp His Asp Tyr Leu Cys Met Ala
            1285            1290            1295

Val Leu Val Gln Glu Ile Ile Asn Ala Asp Tyr Ala Phe Val Ile His
            1300            1305            1310

Thr Thr Asn Pro Ser Ser Gly Asp Asp Ser Glu Ile Tyr Ala Glu Val
            1315            1320            1325

Val Arg Gly Leu Gly Glu Thr Leu Val Gly Ala Tyr Pro Gly Arg Ala
    1330            1335            1340

Leu Ser Phe Ile Cys Lys Lys Asp Leu Asn Ser Pro Gln Val Leu
1345            1350            1355            1360

Gly Tyr Pro Ser Lys Pro Ile Gly Leu Phe Ile Lys Arg Ser Ile Ile
            1365            1370            1375

Phe Arg Ser Asp Ser Asn Gly Glu Asp Leu Glu Gly Tyr Ala Gly Ala
    1380            1385            1390

Gly Leu Tyr Asp Ser Val Pro Met Asp Glu Glu Lys Val Val Ile
    1395            1400            1405

Asp Tyr Ser Ser Asp Pro Leu Ile Thr Asp Gly Asn Phe Arg Gln Thr
    1410            1415            1420

Ile Leu Ser Asn Ile Ala Arg Ala Gly His Ala Ile Glu Glu Leu Tyr
1425            1430            1435            1440

Gly Ser Pro Gln Asp Ile Glu Gly Val Val Arg Asp Gly Lys Ile Tyr
            1445            1450            1455

Val Val Gln Thr Arg Pro Gln Met
            1460

NUCLEIC ACID ENCODING A STARCH R1 PHOSPHORYLATION PROTEIN HOMOLOG FROM MAIZE

CROSS-REFERENCE TO RELATED APPLICATIONS

This is a continuation-in-part of U.S. patent application Ser. No. 09/679,933 abandoned filed Oct. 5, 2000, which is a continuation of International Application No. PCT/US99/07639 filed Apr. 8, 1999, which claims priority benefit of U.S. Provisional Application Ser. No. 60/081,143 filed Apr. 9, 1998.

FIELD OF THE INVENTION

This invention is in the field of plant molecular biology. More specifically, this invention pertains to nucleic acid fragments encoding starch R1 phosphorylation proteins in plants and seeds.

BACKGROUND OF THE INVENTION

Starch is a mixture of two polysaccharides, amylose and amylopectin. Amylose is an unbranched chain of up to several thousand α-D-glucopyranose units linked by α-1,4 glycosidic bonds. Amylopectin is a highly branched molecule made up of up to 50,000 α-D-glucopyranose residues linked by α-1,4 and α-1,6 glycosidic bonds. Approximately 5% of the glycosidic linkages in amylopectin are α-1,6 bonds, which leads to the branched structure of the polymer.

Amylose and amylopectin molecules are organized into granules that are stored in plastids. The starch granules produced by most plants are 15–30% amylose and 70–85% amylopectin. The ratio of amylose to amylopectin and the degree of branching of amylopectin affects the physical and functional properties of the starch. Functional properties, such as viscosity and stability of a gelatinized starch determine the usefulness and hence the value of starches in food and industrial applications.

The R1 protein of potato appears to be a granule associated enzyme that is involved in starch phosphorylation (Lorberth, R. et al. (1998) *Nature Biotechnology* 16:473–477). Nucleic acid fragments encoding starch R1 phosphorylation proteins have been isolated from other species, including rice (PCT International Application No. PCT/EP99/08506) and corn (Patent Application No. DE19653176-A1).

R1 activity has been associated with starch degradation in potato tubers. Studies have shown that inhibition of R1 activity leads to the synthesis of modified starch that is not degraded by enzymes present in potato tissue. If changes in starch degradation are a direct consequence of changes in the degree of phosphorylation this suggests that starch phosphorylation is an important modification that promotes degradation.

Accordingly, the availability of nucleic acid sequences encoding all or a portion of R1 proteins in other plants would facilitate studies to better understand starch degradation and provide genetic tools for the manipulation of starch modification, biosynthesis and metabolism in plant cells.

SUMMARY OF THE INVENTION

The present invention concerns an isolated polynucleotide comprising: (a) a first nucleotide sequence encoding a first polypeptide comprising at least 50 or 100 amino acids, wherein the amino acid sequence of the first polypeptide and the amino acid sequence of SEQ ID NO:6 have at least 80%, 85%, 90%, or 95% identity based on the Clustal alignment method, (b) a second nucleotide sequence encoding a second polypeptide comprising at least 100 amino acids, wherein the amino acid sequence of the second polypeptide and the amino acid sequence of SEQ ID NO:4, SEQ ID NO:8, or SEQ ID NO:14 have at least 90% or 95% identity based on the Clustal alignment method, (c) a third nucleotide sequence encoding a third polypeptide comprising at least 150 amino acids, wherein the amino acid sequence of the third polypeptide and the amino acid sequence of SEQ ID NO:2 have at least 80%, 85%, 90%, or 95% identity based on the Clustal alignment method, (d) a fourth nucleotide sequence encoding a fourth polypeptide comprising at least 150 amino acids, wherein the amino acid sequence of the fourth polypeptide and the amino acid sequence of SEQ ID NO:10 have at least 85%, 90%, or 95% identity based on the Clustal alignment method, (e) a fifth nucleotide sequence encoding a fifth polypeptide comprising at least 350 amino acids, wherein the amino acid sequence of the fifth polypeptide and the amino acid sequence of SEQ ID NO:12 have at least 80%, 85%, 90%, or 95% identity based on the Clustal alignment method, (f) a sixth nucleotide sequence encoding a sixth polypeptide comprising at least 600 amino acids, wherein the amino acid sequence of the sixth polypeptide and the amino acid sequence of SEQ ID NO:20 have at least 80%, 85%, 90%, or 95% identity based on the Clustal alignment method, (g) a seventh nucleotide sequence encoding a seventh polypeptide comprising at least 1337 amino acids, wherein the amino acid sequence of the seventh polypeptide and the amino acid sequence of SEQ ID NO:16 or SEQ ID NO:18 have at least 80%, 85%, 90%, or 95% identity based on the Clustal alignment method, or (h) the complement of the first, second, third, fourth, fifth, sixth, or seventh nucleotide sequence, wherein the complement and the first, second, third, fourth, fifth, sixth, or seventh nucleotide sequence contain the same number of nucleotides and are 100% complementary. The first polypeptide preferably comprises the amino acid sequence of SEQ ID NO:6, the second polypeptide preferably comprises the amino acid sequence of SEQ ID NO:4, SEQ ID NO:8, or SEQ ID NO:14, the third polypeptide preferably comprises the amino acid sequence of SEQ ID NO:2, the fourth polypeptide preferably comprises the amino acid sequence of SEQ ID NO:10, the fifth polypeptide preferably comprises the amino acid sequence of SEQ ID NO:12, the sixth polypeptide preferably comprises the amino acid sequence of SEQ ID NO:20, and the seventh polypeptide preferably comprises the amino acid sequence of SEQ ID NO:16 or SEQ ID NO:18. The first nucleotide sequence preferably comprises the nucleotide sequence of SEQ ID NO:5, the second nucleotide sequence preferably comprises the nucleotide sequence of SEQ ID NO:3, SEQ ID NO:7, or SEQ ID NO:13, the third nucleotide sequence preferably comprises the nucleotide sequence of SEQ ID NO:1, the fourth nucleotide sequence preferably comprises the nucleotide sequence of SEQ ID NO:9, the fifth nucleotide sequence preferably comprises the nucleotide sequence of SEQ ID NO:11, the sixth nucleotide sequence preferably comprises the nucleotide sequence of SEQ ID NO:19, and the seventh nucleotide sequence preferably comprises the nucleotide sequence of SEQ ID NO:15 or SEQ ID NO:17. The first, second, third, fourth, fifth, sixth, and seventh polypeptides preferably are starch R1 phosphorylation proteins.

In a second embodiment, the present invention relates to a chimeric gene comprising any of the isolated polynucleotides of the present invention operably linked to a regulatory sequence.

In a third embodiment, the present invention relates to a vector comprising any of the isolated polynucleotides of the present invention.

In a fourth embodiment, the present invention relates to an isolated polynucleotide fragment comprising a nucleotide sequence comprised by any of the polynucleotides of the present invention, wherein the nucleotide sequence contains at least 30, 40, or 60 nucleotides.

In a fifth embodiment, the present invention relates to an isolated polypeptide comprising: (a) a first amino acid sequence comprising at least 50 or 100 amino acids, wherein the first amino acid sequence and the amino acid sequence of SEQ ID NO:6 have at least 80%, 85%, 90%, or 95% identity based on the Clustal alignment method, (b) a second amino acid sequence comprising at least 100 amino acids, wherein the second amino acid sequence and the amino acid sequence of SEQ ID NO:4, SEQ ID NO:8, or SEQ ID NO:14 have at least 90% or 95% identity based on the Clustal alignment method, (c) a third amino acid sequence comprising at least 150 amino acids, wherein the third amino acid sequence and the amino acid sequence of SEQ ID NO:2 have at least 80%, 85%, 90%, or 95% identity based on the Clustal alignment method, (d) a fourth amino acid sequence comprising at least 150 amino acids, wherein the fourth amino acid sequence and the amino acid sequence of SEQ ID NO:10 have at least 85%, 90%, or 95% identity based on the Clustal alignment method, (e) a fifth amino acid sequence comprising at least 350 amino acids, wherein the fifth amino acid sequence and the amino acid sequence of SEQ ID NO:12 have at least 80%, 85%, 90%, or 95% identity based on the Clustal alignment method, (f) a sixth amino acid sequence comprising at least 600 amino acids, wherein the sixth amino acid sequence and the amino acid sequence of SEQ ID NO:20 have at least 80%, 85%, 90%, or 95% identity based on the Clustal alignment method, or (g) a seventh amino acid sequence comprising at least 1337 amino acids, wherein the seventh amino acid sequence and the amino acid sequence of SEQ ID NO:16 or SEQ ID NO:18 have at least 80%, 85%, 90%, or 95% identity based on the Clustal alignment method. The first amino acid sequence preferably comprises the amino acid sequence of SEQ ID NO:6, the second amino acid sequence preferably comprises the amino acid sequence of SEQ ID NO:4, SEQ ID NO:8, or SEQ ID NO:14, the third amino acid sequence preferably comprises the amino acid sequence of SEQ ID NO:2, the fourth amino acid sequence preferably comprises the amino acid sequence of SEQ ID NO:10, the fifth amino acid sequence preferably comprises the amino acid sequence of SEQ ID NO:12, the sixth amino acid sequence preferably comprises the amino acid sequence of SEQ ID NO:20, and the seventh amino acid sequence preferably comprises the amino acid sequence of SEQ ID NO:16 or SEQ ID NO:18. The polypeptide preferably is a starch R1 phosphorylation protein.

In a sixth embodiment, the present invention relates to a method for transforming a cell comprising introducing any of the isolated polynucleotides of the present invention into a cell, and the cell transformed by this method. Advantageously, the cell is eukaryotic, e.g., a yeast or plant cell, or prokaryotic, e.g., a bacterium.

In a seventh embodiment, the present invention relates to a virus, preferably a baculovirus, comprising any of the isolated polynucleotides of the present invention or any of the chimeric genes of the present invention.

In an eighth embodiment, the invention relates to a method of selecting an isolated polynucleotide that affects the level of expression of a starch R1 phosphorylation protein or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the starch R1 phosphorylation protein or enzyme activity in the host cell containing the isolated polynucleotide; and (d) comparing the level of the starch R1 phosphorylation protein or enzyme activity in the host cell containing the isolated polynucleotide with the level of the starch R1 phosphorylation protein or enzyme activity in the host cell that does not contain the isolated polynucleotide.

In a ninth embodiment, the invention concerns a method of obtaining a nucleic acid fragment encoding a substantial portion of a starch R1 phosphorylation protein, preferably a plant starch R1 phosphorylation protein, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, and 19, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a starch R1 phosphorylation protein amino acid sequence.

In a tenth embodiment, this invention relates to a method of obtaining a nucleic acid fragment encoding all or a substantial portion of the amino acid sequence encoding a starch R1 phosphorylation protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the starch R1 phosphorylation protein polynucleotide in an amount sufficient to complement a null mutant to provide a positive selection means.

In a twelfth embodiment, this invention relates to a method of altering the level of expression of a starch R1 phosphorylation protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the starch R1 phosphorylation protein in the transformed host cell.

BRIEF DESCRIPTION OF THE DRAWING AND SEQUENCE LISTING

The invention can be more fully understood from the following detailed description and the accompanying drawing and Sequence Listing which form a part of this application.

FIGS. 1A, 1B, 1C, 1D, 1E, 1F, and 1G depict an alignment of amino acid sequences of starch R1 phosphorylation protein encoded by the nucleotide sequences derived from corn clone p0126.cnlbz79r (SEQ ID NO:16), a contig assembled from rice clones rlm4n.pk003.p17 and rlr6.pk0099.d9 and PCR fragment sequence (SEQ ID NO:18), and soybean clone scr1c.pk004.n19 (SEQ ID NO:20), and the starch R1 phosphorylation protein from Solanum tuberosum (NCBI GI No. 3287270; SEQ ID NO:21). Amino acids which are conserved among all and at least two sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), sequences of the entire cDNA inserts comprising the indicated cDNA clones ("FIS"), sequences of contigs assembled from two or more ESTs ("Contig"), sequences of contigs assembled from one or more FISs and one or more ESTs or PCR fragment sequence ("Contig*"), or sequences encoding the entire protein derived from an EST, an FIS, a contig, or an FIS and PCR fragment sequence ("CGS"). The sequence descriptions and Sequence Listing attached hereto comply with the rules governing nucleotide and/or amino acid sequence disclosures in patent applications as set forth in 37 C.F.R. §1.821–1.825.

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, or 19, or the complement of such sequences.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. Isolated polynucleotides may be purified from a host cell in

TABLE 1

Starch R1 Phosphorylation Proteins

| | | | SEQ ID NO: | |
|---|---|---|---|---|
| Protein (Plant Source) | Clone Designation | Status | (Nucleotide) | (Amino Acid) |
| Starch R1 Phosphorylation Protein (Arabidopsis) | acs2c.pk001.g20 | EST | 1 | 2 |
| Starch R1 Phosphorylation Protein (Ginger) | ecr1c.pk007.119 | EST | 3 | 4 |
| Starch R1 Phosphorylation Protein (Moss) | emm1c.pk001.p18 | EST | 5 | 6 |
| Starch R1 Phosphorylation Protein (Cattail) | etr1c.pk003.c21 | EST | 7 | 8 |
| Starch R1 Phosphorylation Protein (Rice) | Contig of rlm4n.pk003.p17 r10n.pk088.j11 rlr6.pk0099.d9 (FIS) | Contig* | 9 | 10 |
| Starch R1 Phosphorylation Protein (Soybean) | Contig of scr1c.pk003.e3 ses4d.pk0019.b5 s11.pk0109.f9 s12.pk0041.d7 (FIS) src3c.pk006.d11 (FIS) src3c.pk026.j6 (FIS) | Contig* | 11 | 12 |
| Starch R1 Phosphorylation Protein (Soybean) | scr1c.pk002.k14 | EST | 13 | 14 |
| Starch R1 Phosphorylation Protein (Corn) | p0126.cnlbz79r | CGS | 15 | 16 |
| Starch R1 Phosphorylation Protein (Rice) | Contig of rlm4n.pk003.p17 rlr6.pk0099.d9 (FIS) PCR fragment sequence | CGS | 17 | 18 |
| Starch R1 Phosphorylation Protein (Soybean) | scr1c.pk004.n19 (FIS) | CGS | 19 | 20 | which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, and 19, and the complement of such nucleotide sequences may be used in methods of selecting an isolated polynucleotide that affects the expression of a starch R1 phosphorylation protein in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250, 350, 600, or 1337 amino acids. Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Kienow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptideencoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising: (a) a first nucleotide sequence encoding a first polypeptide comprising at least 50 or 100 amino acids, wherein the amino acid sequence of the first polypeptide and the amino acid sequence of SEQ ID NO:6 have at least 80%, 85%, 90%, or 95% identity based on the Clustal alignment method, (b) a second nucleotide sequence encoding a second polypeptide comprising at least 100 amino acids, wherein the amino acid sequence of the second polypeptide and the amino acid sequence of SEQ ID NO:4, SEQ ID NO:8, or SEQ ID NO:14 have at least 90% or 95% identity based on the Clustal alignment method, (c) a third nucleotide sequence encoding a third polypeptide comprising at least 150 amino acids, wherein the amino acid sequence of the third polypeptide and the amino acid sequence of SEQ ID NO:2 have at least 80%, 85%, 90%, or 95% identity based on the Clustal alignment method, (d) a fourth nucleotide sequence encoding a fourth polypeptide comprising at least 150 amino acids, wherein the amino acid sequence of the fourth polypeptide and the amino acid sequence of SEQ ID NO:10 have at least 85%, 90%, or 95% identity based on the Clustal alignment method, (e) a fifth nucleotide sequence encoding a fifth polypeptide comprising at least 350 amino acids, wherein the amino acid sequence of the fifth polypeptide and the amino acid sequence of SEQ ID NO:12 have at least 80%, 85%, 90%, or 95% identity based on the Clustal alignment method, (f) a sixth nucleotide sequence encoding a sixth polypeptide comprising at least 600 amino acids, wherein the amino acid sequence of the sixth polypeptide and the amino acid sequence of SEQ ID NO:20 have at least 80%, 85%, 90%, or 95% identity based on the Clustal alignment method, (g) a seventh nucleotide sequence encoding a seventh polypeptide comprising at least 1337 amino acids, wherein the amino acid sequence of the seventh polypeptide and the amino acid sequence of SEQ ID NO:16 or SEQ ID NO:18 have at least 80%, 85%, 90%, or 95% identity based on the Clustal alignment method, or (h) the complement of the first, second, third, fourth, fifth, sixth, or seventh nucleotide sequence, wherein the complement and the first, second, third, fourth, fifth, sixth, or seventh nucleotide sequence contain the same number of nucleotides and are 100% complementary. The first polypeptide preferably comprises the amino acid sequence of SEQ ID NO:6, the second polypeptide preferably comprises the amino acid sequence of SEQ ID NO:4, SEQ ID NO:8, or SEQ ID NO:14, the third polypeptide preferably comprises the amino acid sequence of SEQ ID NO:2, the fourth polypeptide preferably comprises the amino acid sequence of SEQ ID NO:10, the fifth polypeptide preferably comprises the amino acid sequence of SEQ ID NO:12, the sixth polypeptide preferably comprises the amino acid sequence of SEQ ID NO:20, and the seventh polypeptide preferably comprises the amino acid sequence of SEQ ID NO:16 or SEQ ID NO:18. The first nucleotide sequence preferably comprises the nucleotide sequence of SEQ ID NO:5, the second nucleotide sequence preferably comprises the nucleotide sequence of SEQ ID NO:3, SEQ ID NO:7, or SEQ ID NO:13, the third nucleotide sequence preferably comprises the nucleotide sequence of SEQ ID NO:1, the fourth nucleotide sequence preferably comprises the nucleotide sequence of SEQ ID NO:9, the fifth nucleotide sequence preferably comprises the nucleotide sequence of SEQ ID NO:11, the sixth nucleotide sequence preferably comprises the nucleotide sequence of SEQ ID NO:19, and the seventh nucleotide sequence preferably comprises the nucleotide sequence of SEQ ID NO:15 or SEQ ID NO:17. The first, second, third, fourth, fifth, sixth, and seventh polypeptides preferably are starch R1 phosphorylation proteins.

Nucleic acid fragments encoding at least a portion of several starch R1 phosphorylation proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other starch R1 phosphorylation protein, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, and 19 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a starch R1 phosphorylation protein, preferably a substantial portion of a plant starch R1 phosphorylation protein, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, and 19, and the complement of such nucleotide sequences; and amplifying a nucleic acid fragment (preferably a cDNA inserted in a cloning vector) using the oligonucleotide primer. The amplified nucleic acid fragment preferably will encode a portion of a starch R1 phosphorylation protein.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of starch phosphorylation in those transgenic plants.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention relates to an isolated polypeptide comprising: (a) a first amino acid sequence comprising at least 50 or 100 amino acids, wherein the first amino acid sequence and the amino acid sequence of SEQ ID NO:6 have at least 80%, 85%, 90%, or 95% identity based on the Clustal alignment method, (b) a second amino acid sequence comprising at least 100 amino acids, wherein the second amino acid sequence and the amino acid sequence of SEQ ID NO:4, SEQ ID NO:8, or SEQ ID NO:14 have at least 90% or 95% identity based on the Clustal alignment method, (c) a third amino acid sequence comprising at least 150 amino acids, wherein the third amino acid sequence and the amino acid sequence of SEQ ID NO:2 have at least 80%, 85%, 90%, or 95% identity based on the Clustal alignment method, (d) a fourth amino acid sequence comprising at least 150 amino acids, wherein the fourth amino acid sequence and the amino acid sequence of SEQ ID NO:10 have at least 85%, 90%, or 95% identity based on the Clustal alignment method, (e) a fifth amino acid sequence comprising at least 350 amino acids, wherein the fifth amino acid sequence and the amino acid sequence of SEQ ID NO:12 have at least 80%, 85%, 90%, or 95% identity based on the Clustal alignment method, (f) a sixth amino acid sequence comprising at least 600 amino acids, wherein the sixth amino acid sequence and the amino acid sequence of SEQ ID NO:20 have at least 80%, 85%, 90%, or 95% identity based on the Clustal alignment method, or (g) a seventh amino acid sequence comprising at least 1337 amino acids, wherein the seventh amino acid sequence and the amino acid sequence of SEQ ID NO:16 or SEQ ID NO:18 have at least 80%, 85%, 90%, or 95% identity based on the Clustal alignment method. The first amino acid sequence preferably comprises the amino acid sequence of SEQ ID NO:6, the second amino acid sequence preferably comprises the amino acid sequence of SEQ ID NO:4, SEQ ID NO:8, or SEQ ID NO:14, the third amino acid sequence preferably comprises the amino acid sequence of SEQ ID NO:2, the fourth amino acid sequence preferably comprises the amino acid sequence of SEQ ID NO:10, the fifth amino acid sequence preferably comprises the amino acid sequence of SEQ ID NO:12, the sixth amino acid sequence preferably comprises the amino acid sequence of SEQ ID NO:20, and the seventh amino acid sequence preferably comprises the amino acid sequence of SEQ ID NO:16 or SEQ ID NO:18. The polypeptide preferably is a starch R1 phosphorylation protein.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded starch R1 phosphorylation protein. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map.

In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization a probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural fraction of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various Arabidopsis (*Arabidopsis thaliana*), ginger (*Curcuma zedoaria*), cattail (*Typha latifolia*), moss (*Brachythecium oxycladon, Plagiomnium cuspidatum, Amblystegium varium*), corn (*Zea mays*), rice (*Oryza saliva*) and soybean (*Glycine max*) tissues were prepared. The characteristics of the libraries are described below.

TABLE 2 cDNA Libraries from Arabidopsis, Ginger, Cattail, Moss, Corn, Rice and Soybean

| Library | Tissue | Clone |
|---|---|---|
| acs2c | Arabidopsis Landsberg erecta fertilized carpels with developing seeds 6–7 days after fertilization | acs2c.pk001.g20 |
| ecr1c | Ginger (*Curcuma zedoaria.* aka shoti starch) developing rhizomes | ecr1c.pk007.119 |
| emm1c | Moss of three variety (*Brachythecium oxycladon, Plagiomnium cuspidatum, Amblystegium varium*) | emm1c.pk001.p18 |
| etr1c | Cattail (*Typha latifolia*) root | etr1c.pk003.c21 |
| r1m4n | Rice Leaf 15 Days After Germination Harvested 2–72 Hours Following Infection With *Magnaporta grisea* (4360-R-62 and 4360-R-67)* | r1m4n.pk003.p17 |
| r10n | Rice (*Oryza sativa* L.) 15 day old leaf* | r10n.pk088.j11 |
| r1r6 | Rice (*Oryza sativa* L.) leaf 15 days after germination, 6 hours after infection of strain *Magaporthe grisea* 4360-R-62 (AVR2-YAMO); Resistant | r1r6.pk0099.d9 |
| scr1c | Soybean (*Glycine max* L., 2872) embryogenic suspension culture subjected to 4 vacuum cycles and collected 12 hrs later | scr1c.pk003.e3 scr1c.pk002.k14 scr1c.pk004.n19 |
| ses4d | Soybean (*Glycine max* L.) embryogenic suspension 4 days after subculture | ses4d.pk0019.b5 |

TABLE 2-continued cDNA Libraries from Arabidopsis, Ginger, Cattail, Moss, Corn, Rice and Soybean

| Library | Tissue | Clone |
|---|---|---|
| s11 | Soybean (*Glycine max* L.) Two week old developing seedlings | s11.pk0109.f9 |
| s12 | Soybean (*Glycine max* L.) two week old developing seedlings treated with 2.5 ppm chlorimuron | s12.pk0041.d7 |
| src3c | Soybean (*Glycine max* L., Bell) 8 day old root inoculated with eggs of cyst nematode *Heterodera glycines* (Race 14) for 4 days. | src3c.pk006.d11 src3c.pk026.j6 |
| p0126 | Corn Leaf Tissue From V8–V10 Stages**, Pooled, Night-Harvested | p0126.cnlbz79r |

*These libraries were normalized essentially as described in U.S. Pat. No. 5,482,845, incorporated herein by reference.
**Corn developmental stages are explained in the publication "How a corn plant develops" from the Iowa State University Coop. Ext. Service Special Report No. 48 reprinted June 1993.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the Saccharomyces cerevisiae Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator Ready reaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding starch R1 phosphorylation protein were identified by conducting BLAST (Basic Local Alignment Search Tool; Altschul et al. (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.*

25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Starch R1 Phosphorylation Protein

The BLASTX search using the EST sequences from clones listed in Table 3 revealed similarity of the polypeptides encoded by the cDNAs to starch R1 phosphorylation protein from Solanum tuberosum (NCBI GenBank Identifier (GI) No. 3287270).

In the process of comparing the ESTs it was found that rice clones rlm4n.pk003.p17, r10n.pk088.j11 and rlr6.pk0099.d9 had overlapping regions of homology. Soybean clones scr1c.pk0032.e3, ses4d.pk0019.b5, s11.pk0109.f9, s12.pk0041.d7, src3c.pk006.d11 and src3c.pk026.j6 were also found to have overlapping regions of homology. Using this homology it was possible to align the ESTs and assemble two individual contigs encoding unique rice and soybean starch R1 phosphorylation proteins.

Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from one or more FISs and one or more ESTs or PCR fragment sequence ("Contig*"), or sequences encoding an entire protein derived from an EST, an FIS, a contig, or an FIS and PCR fragment sequence ("CGS"):

TABLE 3

BLAST Results for Sequences Encoding Polypeptides Homologous to *Solanum tuberosum* Starch R1 Phosphorylation Protein

| Clone | Status | BLAST pLog Score NCBI GI No. 3287270 |
|---|---|---|
| acs2c.pk001.g20 | EST | 62.10 |
| ecr1c.pk007.119 | EST | 75.00 |
| emm1c.pk001.p18 | EST | 56.00 |
| etr1c.pk003.c21 | EST | 53.00 |
| Contig of rlm4n.pk003.p17 r10n.pk088.j11 rlr6.pk0099.d9 (FIS) | Contig* | >250.00 |
| Contig of scr1c.pk003.e3 ses4d.pk0019.b5 s11.pk0109.f9 s12.pk0041.d7 (FIS) | Contig* | >250.00 |

TABLE 3-continued

BLAST Results for Sequences Encoding Polypeptides Homologous to *Solanum tuberosum* Starch R1 Phosphorylation Protein

| Clone | Status | BLAST pLog Score NCBI GI No. 3287270 |
|---|---|---|
| src3c.pk006.d11 (FIS) | | |
| src3c.pk026.j6 (FIS) | | |
| scr1c.pk002.k14 | EST | 94.70 |

The sequence of a portion of the cDNA insert from clone acs2c.pk001.g20 is shown in SEQ ID NO:1; the deduced amino acid sequence of this cDNA, which represents 11% of the protein (middle region), is shown in SEQ ID NO:2. The sequence of a portion of the cDNA insert from clone ecr1c.pk007.119 is shown in SEQ ID NO:3; the deduced amino acid sequence of this cDNA, which represents 9.7% of the protein (middle region) is shown in SEQ ID NO:4. The sequence of a portion of the cDNA insert from clone emm1c.pk001.p18 is shown in SEQ ID NO:5; the deduced amino acid sequence of this cDNA, which represents 10.7% of the protein (middle region) is shown in SEQ ID NO:6. The sequence of a portion of the cDNA insert from clone etr1c.pk003.c21 is shown in SEQ ID NO:7; the deduced amino acid sequence of this cDNA, which represents 7.7% of the protein (middle region), is shown in SEQ ID NO:8.

The sequence of the rice contig composed of clones rlm4n.pk003.p17, r10n.pk088.j11 and rlr6.pk0099.d9 is shown in SEQ ID NO:9; the deduced amino acid sequence of this contig, which represents 33% of the protein (C-terminal region) is shown in SEQ ID NO:10. A calculation of the percent similarity of the amino acid sequence set forth in SEQ ID NO:10 and the *Solanum tuberosum* sequence (NCBI GI No. 3287270; SEQ ID NO:21) (using the Clustal algorithm) revealed that the protein encoded by the contig is 75.1% similar to the *Solanum tuberosum* starch R1 phosphorylation protein.

The sequence of the soybean contig composed of clones scr1c.pk003.e3, ses4d.pk0019.b5, s11.pk0109.f9, s12.pk0041.d7, src3c.pk006.d11 and src3c.pk026.j6 is shown in SEQ ID NO:11; the deduced amino acid sequence of this contig, which represents 40% of the protein (C-terminal region) is shown in SEQ ID NO:12. A calculation of the percent similarity of the amino acid sequence set forth in SEQ ID NO:12 and the *Solanum tuberosum* sequence (NCBI GI No. 3287270; SEQ ID NO:21) (using the Clustal algorithm) revealed that the protein encoded by the contig is 76.4% similar to the *Solanum tuberosum* starch R1 phosphorylation protein. The degree of similarity between the rice (SEQ ID NO:10) and soybean amino acid sequences (SEQ ID NO:12) was calculated to be 70.3% (using the Clustal algorithm).

The sequence of a portion of the cDNA insert from clone scr1c.pk002.k14 is shown in SEQ ID NO:13; the deduced amino acid sequence of this cDNA, which represents 11% of the protein (middle region), is shown in SEQ ID NO:14.

The sequence of the entire cDNA insert in clone rlr6.pk0099.d9 listed in Table 3 was assembled into a contig with nucleotide sequence obtained from corn clone rlm4n.pk003.p17, and a fragment obtained via PCR, to yield nucleotide sequence encoding a full-length starch R1 phosphorylation protein. Further sequencing and searching of the DuPont proprietary database allowed the identification of a corn clone and another soybean clone encoding starch R1 phosphorylation protein. The BLASTX search using the EST sequences from clones listed in Table 4 revealed similarity of the polypeptides encoded by the cDNAs to starch R1 phosphorylation protein from *Solanum tuberosum* (NCBI GI Nos. 3287270 and 7489244). Shown in Table 4 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from one or more FISs and one or more ESTs or PCR fragment sequence ("Contig*"), or sequences encoding the entire protein derived from an EST, an FIS, a contig, or an FIS and PCR fragment sequence ("CGS").

TABLE 4

BLAST Results for Sequences Encoding Polypeptides Homologous to *Solanum tuberosum* Starch R1 Phosphorylation Protein

| Clone | Status | BLAST Results NCBI GI No. | BLAST pLog Score |
|---|---|---|---|
| p0126.cnlbz79r | CGS | 7489244 | >180.00 |
| Contig of r1m4n.pk003.p17 r1r6.pk0099.d9 (FIS) PCR fragment sequence | CGS | 3287270 | >180.00 |
| scr1c.pk004.n19 (FIS) | CGS | 3287270 | >180.00 |

FIGS. 1A–1G present an alignment of the amino acid sequences set forth in SEQ ID NOs:16, 18, and 20 and the *Solanum tuberosum* sequence (NCBI GI No. 3287270; SEQ ID NO:21). The data in Table 5 represents a calculation of the percent identity of the amino acid sequences set forth in SEQ ID NOs:16, 18, and 20 and the *Solanum tuberosum* sequence (NCBI GI No. 3287270; SEQ ID NO:21).

TABLE 5

Percent Identity of Amino Acid Sequences Deduced From the Nucleotide Sequences of cDNA Clones Encoding Polypeptides Homologous to *Solanum tuberosum* Starch R1 Phosphorylation Protein

| SEQ ID NO. | Percent Identity to NCBI GI No. 3287270; SEQ ID NO:21 |
|---|---|
| 16 | 64.2 |
| 18 | 64.3 |
| 20 | 68.4 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Sequence alignments and BLAST scores and probabilities indicate that the nucleic acid fragments comprising the instant cDNA clones encode a substantial portion of a starch R1 phosphorylation protein. These sequences represent the first arabidopsis, ginger, moss, cattail, rice and soybean sequences encoding starch R1 phosphorylation protein known to Applicant. A nucleic acid fragment that encodes starch R1 phosphorylation protein has been previously isolated from corn (Patent Application No. DE19653176-A1).

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having starch R1 phosphorylation activity, wherein the amino acid sequence of the polypeptide comprises the amino acid sequence of SEQ ID NO:16, or
   (b) the complement of the nucleotide sequence of (a), wherein the complement and the nucleotide sequence consist of the same number of nucleotides and are 100% complementary.

2. The polynucleotide of claim 1, wherein the nucleotide sequence comprises the nucleotide sequence of SEQ ID NO:15.

3. A vector comprising the polynucleotide of claim 1.

4. A recombinant DNA construct comprising the polynucleotide of claim 1 operably linked to at least one regulatory sequence.

5. A method for transforming a cell comprising transforming a cell with the polynucleotide of claim 1.

6. A cell comprising the recombinant DNA construct of claim 4.

7. A method for producing a plant comprising transforming a plant cell with the polynucleotide of claim 1 and regenerating a plant from the transformed plant cell.

8. A plant comprising the recombinant DNA construct of claim 4.

9. A seed comprising the recombinant DNA construct of claim 4.

10. A method for isolating a polypeptide having starch R1 phosphorylation activity, wherein the method comprises:
    transforming a cell with the recombinant DNA construct of claim 4;
    growing the cell in culture medium; and
    isolating the polypeptide from the cell or the culture medium.

* * * * *